(12) United States Patent
Baxter et al.

(10) Patent No.: US 7,302,347 B2
(45) Date of Patent: Nov. 27, 2007

(54) METHOD FOR CREATING SPECIFIC, HIGH AFFINITY NUCLEAR RECEPTOR PHARMACEUTICALS

(75) Inventors: John D. Baxter, San Francisco, CA (US); Thomas S. Scanlan, San Francisco, CA (US); Robert J. Fetterick, Hillsborough, CA (US); Sabine Borngraeber, San Francisco, CA (US); Paul Webb, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 503 days.

(21) Appl. No.: 10/317,034

(22) Filed: Dec. 10, 2002

(65) Prior Publication Data

US 2004/0110154 A1  Jun. 10, 2004

(51) Int. Cl.
  G01N 33/53 (2006.01)
  G06G 7/48 (2006.01)
(52) U.S. Cl. .......................... 702/19; 702/20; 703/11; 707/102; 435/7.1
(58) Field of Classification Search ............ 702/19–20; 707/102; 703/11
See application file for complete search history.

(56) References Cited

U.S. PATENT DOCUMENTS

| | | | | |
|---|---|---|---|---|
| 5,883,294 A | * | 3/1999 | Scanlan et al. | 562/471 |
| 6,107,517 A | * | 8/2000 | Scanlan et al. | 562/471 |
| 6,236,946 B1 | * | 5/2001 | Scanlan et al. | 702/22 |
| 6,266,622 B1 | | 7/2001 | Scanlan et al. | |
| 6,410,245 B1 | * | 6/2002 | Northrop et al. | 435/7.1 |
| 6,639,078 B1 | * | 10/2003 | Haffner et al. | 546/272.1 |
| 6,689,574 B1 | * | 2/2004 | Cummings et al. | 435/7.8 |
| 2002/0037514 A1 | | 3/2002 | Klein et al. | |
| 2002/0137794 A1 | | 9/2002 | Evans et al. | |

FOREIGN PATENT DOCUMENTS

WO  99/50658  * 10/1999

OTHER PUBLICATIONS

Baxter, J.D. et al. J of Steroid Biochemistry & Molecular Biology (Mar. 2001) 76 :31.*
Webb et al. (2003) J of Steroid Biochem & mol. Biol. 83:59.*
Chiellini et al., "Synthesis and Biological Activity of Novel Thyroid Hormone Analogues: 5'-Aryl Substituted GC-1 Derivatives", Bioorganic & Medicinal Chemistry, (2002) vol. 10:333-346.
Yen (2001) "Physiological and Molecular Basis of Thyroid Hormone Action" Physiological Reviews 81(3):1097-1142.
Bourguet et al. (1995) "Crystal Structure of the ligand binding domain of the human nuclear receptor RXR-alpha" Nature 375:377-382.
Renaud et al. (1995) "Crystal Structure of the RAR-gamma ligand binding domain bound to all-trans retinoic acid"; Nature 378:681-689.
Wagner et al. (1995) "A structural Role for hormone in the thyroid hormone receptor" Nature 378:690-697.
Brzozowski et al. (1997) "Molecular Basis of Agonism and Antagonism in the Oestrogen Receptor" Nature 389:753-758.
Darimont et al. (1998) "Structure and Specificity of Nuclear Receptor-Coactivator Interactions." Genes Dev 12:3343-3356.
Feng et al. (1998) "Hormone Dependent Coactivator Binding to a Hydrophobic Cleft on Nuclear Receptors" Science 280:1747-1749.
Marimuthu et al (2002) "Thyroid Hormone Receptor Surfaces and Conformations Required to Bind Nuclear Receptor Corepressor (N-CoR)" Mol Endocrinol 16:271-86.
Shibata et al. (1997) Recent Progress in Hormone Res. 52:141-164.
Tagami, et al. (1997) "Nuclear receptor corepressors activate rather than suppress basal transcription of genes that are negatively regulated by thyroid hormone."Mol. Cell Biol. 17(5):2642-2648.
Zhu et al. (1997) "The Differential Hormone-dependent Transcriptional Activation of Thyroid Hormone Receptor Isoforms Is Mediated by Interplay of Their Domains" J. Biol. Chem. 272(14):9048-9054.
Lin et al. (1997) "A conformational switch in nuclear hormone receptor is involved in coupling hormone binding to corepressor release." Mol. Cell Biol. 17(10):6131-6138.
Kakizawa et al. (1997) "Ligand-dependent heterodimerization of thyroid hormone receptor and retinoid X receptor." J. Biol. Chem. 272(38):23799-23804.
Chang, K. H., et al. (1997) "A thyroid hormone receptor coactivator negatively regulated by the retinoblastoma protein." Proc. Natl. Acad. Sci. USA 94(17):9040-9045.
Wijayaratne et al (1999) "Comparative analyses of mechanistic differences among antiestrogens." Endocrinology 140(12):5828-5840.
Chang, C.Y., et al (1999) "Dissection of the LXXLL nuclear receptor-coactivator interaction motif using combinatorial peptide libraries: discovery of peptide antagonists of estrogen receptors alpha and beta."Mol. Cell Biol 19(12):8226-8239.
Norris et al (1999) "Peptide Antagonists of the Human Estrogen Receptor" Science 285:744-746.
Paige et al (1999) "Estrogen receptor (ER) modulators each induce distinct conformational changes in ER α and ER β" Proc. Natl. Acad. Sci. USA 96:3999-4004.

* cited by examiner

Primary Examiner—Mary K. Zeman
(74) Attorney, Agent, or Firm—Quine I.P. Law Group; Paul Littlepage

(57) ABSTRACT

This invention pertains to agonists that activate nuclear receptors. These agonists include an extension that contacts a region of the nuclear receptor outside the native ligand binding pocket. Methods for producing, identifying and designing such agonists are included along with nuclear receptor agonist complexes and libraries of agonists.

24 Claims, 6 Drawing Sheets
(4 of 6 Drawing Sheet(s) Filed in Color)

5'-aryl (GC series) or methylene bridge (HY-4) substituted GC-1 analogs

Most compounds have agonist activity; boxed compounds have antagonist activity

METHOD FOR CREATING SPECIFIC, HIGH AFFINITY NUCLEAR RECEPTOR PHARMACEUTICALS

STATEMENT AS TO RIGHTS TO INVENTIONS MADE UNDER FEDERALLY SPONSORED RESEARCH AND DEVELOPMENT

The invention was made with United States Government support under grant numbers DK41842, DK09516, DK53417, and DK52798 from the National Institutes of Health. The United States Government has certain rights in the invention.

CROSS-REFERENCE TO RELATED APPLICATIONS

Not Applicable

FIELD OF THE INVENTION

The present invention is in the field of ligand design for agonists of nuclear receptors. The invention also relates to ligand-receptor complexes, screening methods for nuclear receptor agonists, libraries of nuclear receptor agonists and methods of treating diseases with nuclear receptor agonists.

BACKGROUND OF THE INVENTION

Nuclear receptors represent a superfamily of proteins that specifically bind physiologically relevant small molecules, such as hormones, vitamins, fatty acids or the like. Binding of an agonist to a nuclear receptor, induces the receptor to modulate transcription in the cell in a positive or negative way (the receptor-agonist complex can have transcription independent actions as well.). Unlike integral membrane receptors and membrane associated receptors, nuclear receptors mostly reside in either the cytoplasm or nucleus of eukaryotic cells. Thus, nuclear receptors comprise a class of intracellular, soluble, ligand-regulated transcription factors.

The biology and physiology of several nuclear receptors has been worked out in some detail. For example, the physiological and molecular basis of thyroid hormone action is reviewed in Yen (2001) *"Physiological and Molecular Basis of Thyroid Hormone Action" Physiological Reviews* 81(3):1097-1142, and the references cited therein. Known and well characterized nuclear receptors include those for glucocorticoids (GRs), androgens (ARs), mineralocorticoids (MRs), progestins (PRs), estrogens (ERs), thyroid hormones (TRs), vitamin D (VDRs), retinoids (RARs and RXRs), and the peroxisome proliferator activated receptors (PPARs) that bind eicosanoids. The so called "orphan receptors" are also part of the nuclear receptor superfamily, as they are structurally homologous to classic nuclear receptors, such as steroid and thyroid receptors. Ligands have not been identified for orphan receptors but it is likely that small molecule ligands will be discovered in the near future for many of this class of transcription factors. Generally, nuclear receptors specifically bind physiologically relevant small molecules with high affinity. Apparent Kd's are commonly in the 0.01-20 nM range, depending on the nuclear receptor/ligand pair.

Nuclear receptors are involved in a myriad of physiological processes and medical conditions such as hypertension, heart failure, atherosclerosis, inflammation, immunomodulation, hormone dependent cancers (e.g. breast, thyroid, and prostate cancer), modulation of reproductive organ function, hyperthyroidism, hypercholesterolemia and other abnormalities of lipoproteins, diabetes, osteoporosis, mood regulation, mentation, and obesity. Consequently, it is advantageous to develop ligands to nuclear receptors with desired properties, e.g., activating the receptor, deactivating the receptor, etc.

Certain progress has been made in this regard. For example, U.S. Pat. No. 5,883,294 by Scanlan et al. (SELECTIVE THYROID HORMONE ANALOGUES) describes, e.g., several classes of artificial thyroid hormone receptor ligands. Similarly, U.S. Pat. No. 6,266,622 by Scanalan et al. (NUCLEAR RECEPTOR LIGANDS AND LIGAND BINDING DOMAINS) also describes several classes of thyroid hormone receptor ligands. For example, superagonists are described in the '622 patent, in which, e.g., the interactions of the ligand with various receptor residues (e.g., Arg 262, Arg 266 and Arg 228) in the ligand binding pocket are optimized. The '622 patent also provides methods of designing antagonists to thyroid hormone and other nuclear receptors, via the extension hypothesis, which provides, in part, that various bulky extension groups on receptor ligands confer antagonistic activity to the ligand. For example, extension groups that project towards the C terminal helix of the receptor, when the ligand is bound to the receptor, can provide antagonist activity.

The present invention derives, in part, from the surprising discovery that certain extension groups can be used in agonist design. This and many other features of the invention, will become apparent upon review of the following.

SUMMARY OF THE INVENTION

The invention derives, in part, from the surprising discovery that nuclear receptor agonists can comprise bulky extension regions, and that these extension regions can alter (increase or decrease) specificity and/or affinity of the agonist for the receptor. Thus, the present invention provides methods for producing agonists, nuclear receptor-agonist complexes, including various crystal structures thereof, therapeutic methods and compositions and several associated features such as kits. For example, agonists that have a higher specificity or affinity for a receptor than the native ligand are provided by the present invention. This is a significant advance in the field, because, for example, different receptor isoforms are relevant to different diseases and the ability to selectively activate one isoform over another can provide for more diseases-specific treatment.

Accordingly, in a first aspect, the invention provides methods of producing an agonist for a nuclear receptor (and/or the agonists produced by the methods). For example, a modified nuclear receptor ligand comprising an extension is provided, where the extension contacts a region of the nuclear receptor outside of a native ligand binding pocket of the receptor. The modified nuclear receptor ligand is confirmed to have agonist activity on the nuclear receptor, thereby producing the agonist.

In a closely related aspect, the invention provides methods of producing an agonist for a nuclear receptor (and/or the agonists produced by the methods), in which the methods include providing a modified nuclear receptor ligand comprising means for contacting a region of the nuclear receptor outside of a native ligand binding pocket of the nuclear receptor, and confirming that the modified nuclear receptor ligand comprises agonist activity on the nuclear receptor, thereby producing the agonist.

In yet an additional closely related aspect of the invention, methods of identifying one or more agonist for a nuclear receptor (and/or the agonists produced by the methods) are provided. In the methods, a plurality of putative agonists are provided, each comprising an extension, wherein the extension contacts a region of the nuclear receptor outside of the native ligand binding pocket. The putative agonists are tested for agonist activity on the nuclear receptor, thereby identifying the one or more agonists of the nuclear receptor.

In another closely related class of methods, methods of identifying one or more agonist for a nuclear receptor (and the agonists identified by the method) are provided. In the methods, a plurality of putative agonists are provided, each comprising means for contacting a region of the nuclear receptor outside of the native ligand binding pocket, and the putative agonists are tested for agonist activity on the nuclear receptor, thereby identifying the one or more agonists of the nuclear receptor.

One aspect of the invention comes from the surprising discovery that nuclear hormone receptors with bulky side groups can comprise agonistic activity, rather than antagonistic activity. Accordingly, one additional feature of the invention is a method of identifying a nuclear hormone receptor agonist by screening a putative nuclear hormone receptor antagonist comprising an extension for agonistic activity on a nuclear hormone receptor.

The invention additionally provides methods of designing a putative agonist for a nuclear receptor. In the methods, a three dimensional model of a protein or polypeptide comprising a nuclear receptor ligand binding pocket of the nuclear receptor is provided. Binding of one or more compounds to the three dimensional model is modeled, in which each compound comprises an extension that spatially fits into a contact region outside the ligand binding pocket of the protein and does not substantially disrupt a coactivator binding surface of the receptor, thereby designing the putative agonist. This, in turn, provides methods of designing a protein ligand for a nuclear receptor using information provided by the crystal structure (e.g., for rational ligand design approaches using models that take the crystal structure information into account). For example, in the methods, an information set derived from the crystal structure of thyroid hormone bound to GC-24 is accessed, and, based on information in the information set, a prediction is made regarding whether a putative ligand will interact with one or more three dimensional features of a nuclear receptor, e.g., to provide agonist activity to the receptor (e.g., binding that does not disrupt the coactivator binding surface of the nuclear receptor is modeled using any available modeling tool and the crystal structure of the invention). For example, the information set can include atomic coordinate information of Table 2, or graphical modeling of that data, e.g., as provided by the various figures herein. Similarly, systems that include an information storage module and an information set derived from a crystal structure of thyroid hormone bound to GC-24 are a feature of the invention. In a related aspect, crystals of nuclear hormone receptors (e.g., thyroid receptor) and GC-24 are also a feature of the invention.

In addition to providing agonists produced by any of the methods above (or combinations thereof), the invention also provides a nuclear receptor agonist complex composition that includes a nuclear receptor bound to an agonist, wherein the agonist comprises an extension that contacts a region of the nuclear receptor outside of a native ligand binding pocket. This complex can be identified by the methods above, or by any other method. In a closely related aspect, a nuclear receptor agonist complex comprising a nuclear receptor bound to an agonist is provided, in which the agonist comprises means for contacting a region of the nuclear receptor outside of a native ligand binding pocket.

Libraries comprising a plurality of different agonists produced by any of the methods herein are also a feature of the invention. In an additional related aspect, the invention provides libraries of agonists for a nuclear receptor, where the library comprises a plurality of different agonists, where a plurality of the different agonists comprise a nuclear receptor ligand with an extension that contacts a region of the nuclear receptor outside of a native ligand binding pocket. Typically, though not necessarily, at least about 50% (and often about 80%, about 90%, or about 95% or more) of the plurality of different agonists comprising a nuclear receptor ligand with an extension. The libraries can be formatted as agonist-receptor complexes, or as agonists. The libraries can be spatially organized (e.g., in a gridded array) or can exist in any other logically accessible format.

For any of the above methods or compositions (including any agonist, agonist-receptor complex, library thereof or any other composition of the invention noted herein), the extension of the modified nuclear receptor ligand typically spatially fits into the region of the receptor without substantially disrupting a coactivator binding surface of the nuclear receptor (receptor ligands that disrupt the binding surface typically display antagonist activity, rather than agonist activity, because disruption if the binding surface typically inhibits one or more activity of the receptor). One example coactivator binding surface is formed by one or more of helices 3, 4, 5, 6 and 12 of the nuclear receptor. In one embodiment, the coactivator binding surface is formed by helices 3, 4, 5, 6 and 12.

For any or all of the above methods or compositions, several example agonists identified/modeled by the methods above, or that can be used in the above compositions are provided herein, including agonists where the region of the nuclear receptor comprises a domain formed, at least in part, by helices 3 and 11 of the nuclear receptor. The extension itself can be any of a variety of structures that have sufficient size to project outwards from the ligand binding pocket of the receptor. For example, the extension can include a —XR moiety, e.g., where the X is a $CH_2$, an O, a S, a NH, a NR", a CHR", or a CR"$_2$. In this embodiment, R" is H or a lower alkyl, R being a phenyl, a 5-member heterocyclic ring, a 6-member heterocyclic ring, a substituted phenyl, a substituted 5-member heterocyclic ring, or a substituted 6-member heterocyclic ring. Typically, the extension is greater than about 50 Daltons in size and less than about 500 Daltons in size. In one common class of examples, the extension comprises at least 3 carbons. The agonist ligand and/or the extension can be purely synthetic, or can be partly or completely naturally occurring. Similarly, the agonist and or extension can be made via chemical synthesis, biological synthesis or a combination thereof. The agonist ligand can be synthesized from scratch, or by modular synthesis strategies, e.g., by providing a first ligand (e.g., a native ligand) and coupling an extension (or part of an extension) to it to produce the agonist ligand that comprises the extension.

An example of an agonist producible by the methods of the invention is GC-24 (of course, an agonist of the invention is optionally an agonist other than GC-24). Considerable structural information is provided herein regarding the use of GC-24 and related molecules as agonists, including a crystal structure of GC-24 bound to thyroid hormone receptor (TR). Accordingly, complexes of the invention can include GC-24 agonists, structurally related agonists or structurally unrelated agonists. Examples of structurally related agonists include molecules derived from the chemical structure of GC-1 with an extension, e.g., a benzyl moiety located at a 3' position of an aryl ring in the chemical structure of GC-1.

For any of the methods or compositions above, agonist activity of the relevant agonist typically comprises activation of the nuclear receptor, e.g., providing modulation of transcription of at least one nuclear receptor responsive gene. Typical associated transcription modulatory activities can include, e.g., dissociation of heat shock protein from the nuclear receptor, dimerization of the nuclear receptor, dissociation of one or more transcriptional repressor or other regulatory proteins from the nuclear receptor and/or any other activity typical to an activated nuclear receptor.

Generally, the agonist activity of a ligand can be confirmed in any of the methods of the invention, or for any of the compositions of the invention by any of a variety of methods, e.g., by binding the modified nuclear receptor ligand to the nuclear receptor and testing for agonist activity, or by another appropriate activity assay, in vitro or in vivo. For example, the agonist or complex produced by binding of the agonist to the receptor can be in a cell-free in vitro system (e.g., a transcription/translation system), or in a cell, or in a mammal. In one example, testing for agonist activity includes binding the plurality of putative agonists to the nuclear receptor, selecting for members of the plurality of putative agonists that bind the nuclear receptor and testing the resulting ligand bound nuclear receptors for agonist activity. Any of these steps can be performed in vitro, or in vivo, or in any combination thereof.

Any of a variety of nuclear receptors can be used in the methods and compositions of the present invention, including a thyroid hormone receptor, a β thyroid hormone receptor, an alpha thyroid hormone receptor, a glucocorticoid receptor, an estrogen receptor, an androgen receptor, a mineralocorticoid receptor, a progestin receptor, a vitamin D receptor, a retinoid receptor, a retinoid X receptor, a peroxisomal proliferator activated receptor, an estrogen-receptor related receptor, a short heterodimer partner, a constitutive androstane receptor, a liver X receptor (LXR), a pregnane X receptor, a HNF-4 receptor, a farnesoid X receptor (FXR) and an orphan receptor. Nuclear receptors can include nuclear receptors expressed by human and non-human species including vertebrates and invertebrates. A database of nuclear receptors is available on the World Wide Web at receptors.ucsf.edu/NR/multali/multali.html. The invention can utilize any isoform of the relevant receptors—indeed, given that the present invention provides the ability to make agonists that have increased specificity, the agonists of the invention can be used to differentiate between different isoforms (agonists can be selected to have different activity on different isoforms of a given receptor). This is particularly useful to target nuclear receptor isoform-specific diseases.

The present invention also provides methods of treatment, e.g., using any of the agonists of the invention, e.g., as identified by any of the methods above. For example, the invention provides methods of treating a subject having a disease state which is alleviated by treatment with a nuclear receptor agonist, in which a therapeutically effective amount of an agonist of the invention is administered to the subject (e.g., a human or, in a veterinary application, an animal such as a mammal) in need of treatment. For example, in one therapeutic application, the agonist binds a thyroid hormone receptor. In one typical class of embodiments, the agonist is mixed with one or more pharmaceutically acceptable excipients prior to administration.

Example diseases that can be treated using the agonists of the invention include, but are not limited to: hyperchloesterolemia, atherosclerosis, obesity, cardiac arrhythmia, modulation of reproductive organ function, hypothothyroidism, osteoporosis, hypertension, cancer, thyroid cancer, breast cancer, prostate cancer, glaucoma, and/or depression.

Kits comprising any composition of the invention are also a feature of the invention. Kits typically comprise one or more composition of the invention, e.g., packaged in one or more containers. The kits optionally provide instructions, e.g., for practicing one or more method herein.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" includes a combination of two or more surfaces; reference to "bacteria" includes mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the invention, the preferred materials and methods are described herein. In describing and claiming the present invention, the following terminology will be used in accordance with the definitions set out below.

An "agonist for a nuclear receptor" is an agent that, when bound to the nuclear receptor, activates nuclear receptor activity to activate or repress gene function. In some cases, nuclear receptors can act through second messenger signaling pathways, and the invention would apply to these actions as well. The activation can be similar in degree to that provided by a natural hormone for the receptor, or can be stronger (optionally referred to as a "strong agonist"), or can be weaker (optionally referred to as a "weak agonist" or "partial agonist"). An example of a hormone for a nuclear receptor is thyroid hormone, which is a natural hormone for the thyroid receptor. A "putative agonist" is an agent to be tested for agonist activity.

An "antagonist for a nuclear receptor" is an agent that reduces or blocks activity mediated by the receptor in response to an agonist of the receptor. The activity of the antagonist can be mediated, e.g., by blocking binding of the agonist to the receptor, or by altering receptor configuration and/or activity of the receptor. A "putative antagonist" is an agent to be tested for antagonist activity.

A "modified nuclear receptor ligand" is a molecule, other than the natural cognate ligand for the nuclear receptor that binds to the nuclear receptor. The modified nuclear receptor ligand can be naturally occurring or artificial. It can be synthesized via in vitro chemical synthesis approaches or via in vitro or in vivo biological synthesis, or any combination thereof.

An "extension," in the context of a nuclear receptor ligand, is that portion of the nuclear receptor ligand that does not fit within the standard native ligand binding pocket for the receptor. For example, the extension can contact regions outside of the binding pocket, such as domains of the nuclear receptor present in helices, e.g., 3 and 11, or 3, 11 and 12, of the thyroid hormone receptor.

A "native ligand" for a receptor (also termed a "native receptor ligand") is a natural cognate ligand for that receptor. For example, cortisol is a native ligand for the glucocorticoid receptor, while 3,5,3'-triiodo-L-thyronine (triiodothyronine, $T_3$ or thyroid hormone) is a native ligand for the thyroid hormone receptor.

A "native ligand binding pocket" is the structural portion of the receptor that fits into close proximity or contact with the natural cognate ligand for the receptor. Thus, the native ligand binding pocket is the structural pocket formed by the receptor when it binds to the natural cognate ligand for the receptor.

The term "spatially fits" in the context of a ligand binding to a receptor feature (e.g., a ligand binding pocket) means that the ligand is contained within the feature.

A "thyroid hormone receptor" is a protein that is the same as or is similar to a known thyroid hormone receptor, wherein the protein is activated by thyroid hormone. Typically, if the protein is similar to the known receptor, it is more similar to a known thyroid receptor than it is to another identified receptor type. Known receptors that are annotated as being members of a given family of receptors can be found in GenBank or other public databases, e.g., a database of nuclear receptors is available on the World Wide Web at receptors.ucsf.edu/NR/multali/multali.html. Similarly, a "glucocorticoid receptor" is a protein that is the same as or similar to a known glucocorticoid receptor, where the protein binds a glucocorticoid such as cortisol. In general, a given nuclear hormone receptor type is a protein that is the same as or similar to a given nuclear hormone receptor type that is activated by the relevant natural cognate ligand. In all cases, the receptor may be activated by other ligands as well. Indeed, because of this receptor-ligand cross-talk, it is not formally correct to identify a receptor based simply upon which hormone(s) it binds to—for example, the mineralcorticoid receptors bind cortisol (a glucocorticoid). Thus, a receptor is defined based upon its degree of similarity to a known receptor that has been identified as a given receptor type (typically, the known receptor is initially named based upon its primary hormone binding activity) and upon whether it is activated in response to a given hormone. In this context, the degree of similarity that can be used to identify the receptor is somewhat flexible—many receptors are homologous to one another, showing at least some degree of similarity. Typically, a receptor is fit into a given family of receptors (e.g., the family of thyroid receptors) based upon how closely similar it is to other members of the family as compared to other receptor families and upon its ligand specificity. One can group receptor families into branches of an evolutionary tree to show relationships between family members and/or between families. Many software programs are publicly available for performing sequence similarity comparisons, including BLAST, BESTFIT, FASTA and many others. For a review of available sequence alignment and clustering methods and tools see also, Durbin et al. (1998) *Biological Seciuence Analysis: Probabilistic Models of Proteins and Nucleic Acids* Cambridge University Press; and Mount (2001) *Bioinformatics Sequence and Genome Analysis* Cold Spring Harbor Press.

A "nuclear receptor" is a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound.

Unless otherwise specified, "in vitro" implies that something takes place outside of an organism or cell. "In vivo" implies that it takes place inside of a cell (the cell can be in culture or in a tissue, or an organism, or the like).

A "nuclear receptor responsive gene" is a gene whose transcription is altered in a cell in response a nuclear receptor. The receptor can modulate the activity of the gene in the absence of the nuclear ligand, sometimes in response to second messenger signaling pathways, and activation of the receptor by binding of an agonist ligand can modulate the receptor to differ in its activation or repression of the gene. The receptor can act while bound to DNA or while bound to other proteins directly or indirectly involved in transcription of the gene. The activity of the nuclear receptor responsive gene could also be modulated through nuclear receptor effects on second messenger signaling pathways.

GC-24 is a compound having the formula:

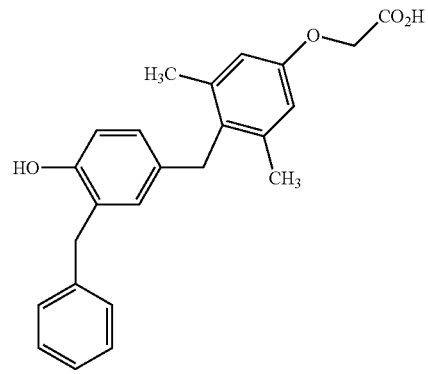

or a salt or ion thereof.

The term "test agent" refers to an agent (e.g., a putative agonist) that is to be screened in one or more of the assays described herein. The agent can be essentially any compound. It can exist as a single isolated compound or can be a member of a chemical (e.g. combinatorial) library.

A "library" is a set of compounds or compositions. It can take any of a variety of forms, e.g., comprising spatial organization (e.g., an array, e.g., a gridded array), or logical organization (e.g., as existing in a database, e.g., that can locate compounds or compositions in an external storage system).

The term "database" refers to a means for recording and retrieving information. In preferred embodiments, the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases, e.g., those used to track agonist or antagonist activity (or putative agonist or antagonists during the various screening processes herein). Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

The phrases "an amount [of an agent, e.g., an agonist or antagonist of a nuclear receptor] sufficient to maintain changes in gene expression" or "an amount sufficient to induce changes in gene expression" refers to the amount of the "agent" sufficient maintain or induce those changes in the subject organism as empirically determined or as extrapolated from an appropriate model system.

A "therapeutically effective amount of an agonist" is an amount of the agonist that is sufficient to provide a beneficial therapeutic effect, typically when administered over time.

A "therapeutically effective amount of an antagonist" is an amount of the antagonist that is sufficient to provide a beneficial therapeutic effect, typically when administered over time.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that can have alternate backbones, comprising, for example, phosphoramide (Beaucage et al. (1993) *Tetrahedron* 49(10): 1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110: 4470; Letsinger et al. (1994) *Nucleoside & Nucleotide* 13:1597; Chapters 2 and 3, *ASC Symposium Series* 580, "*Carbohydrate Modifications in Antisense Research*", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, *ASC Symposium Series* 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169-176). Several nucleic acid analogs are described in Rawls, *C & E News* Jun. 2, 1997 page 35. These modifications of the ribose-phosphate backbone can be done to facilitate the addition of additional moieties such as labels, or to increase the stability and half-life of such molecules in physiological environments.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

DETAILED DESCRIPTION

Introduction

Figure 1:
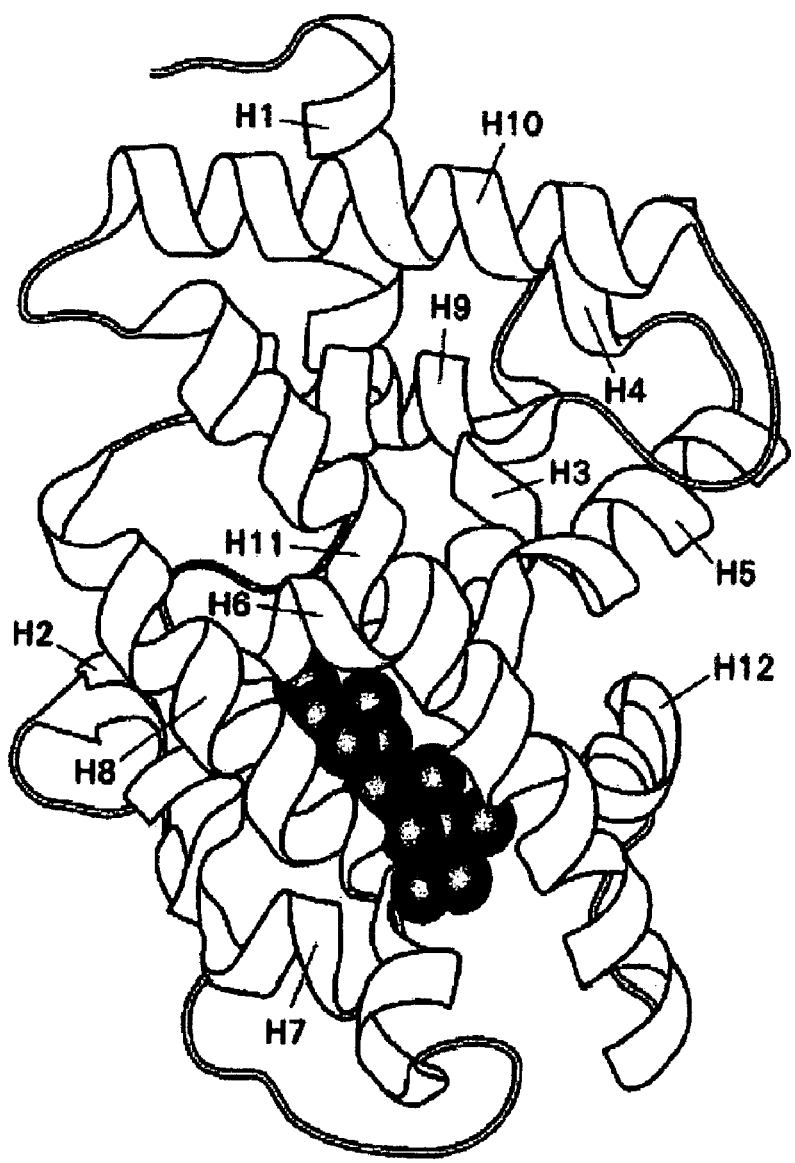
FIG. 1 schematically illustrates a TRα-1 ligand binding domain crystal structure.

20% of prescribed drugs in the United States are ligands for nuclear receptors. Recent developments in nuclear receptor structure-function illuminate the roles of these receptors in cardiovascular disease, obesity, diabetes, drug metabolism, bone disease, cancer and other diseases. An important goal in the field is the identification of novel small molecules that activate or inhibit the actions of nuclear receptors in specified physiological venues. However, efforts to produce new compounds are hampered by problems with low receptor affinity, cross-reactivity between similar receptors and difficulty in predicting the effects of the compounds upon receptor activity. Cross-reactivity is particularly important, given the increasing efforts in developing ligands that are specific for receptor isoforms; in these cases, the receptors have very few structural differences. As discussed above, the present invention provides new ways of increasing the specificity of ligands of interest, i.e., by adding extensions to a ligand that contact the regions of the receptor that are outside (e.g., distinct) the ligand binding pocket and yet allow the receptor to fold in such a way to form the coactivator-binding surface. In this way, the specificity of ligand-receptor binding can be increased.

The invention provides methods and for producing, identifying, and/or designing, ligands, e.g., agonists, for nuclear receptors along with nuclear receptor agonist complexes and libraries of agonists. Compositions of these agonists with a nuclear receptor, along with libraries of agonists are also provided. Agonists or putative agonists of the invention comprise one or more extensions, in addition to a portion that binds within the binding pocket of the receptor. This extension contacts a region of the nuclear receptor outside of a native ligand binding pocket of the receptor and confers agonist activity.

Nuclear receptor interacting ligands can be classified agonists, partial agonists-partial antagonists, antagonists, mixed agonist-antagonists or inverse agonists. The effects of compounds vary in different tissues and with respect to the factors that interact with hormone-responsive genes. Thus, the same compound in one tissue or context can act differently in another context.

An agonist binds to a receptor and transmits binding into a response. For example, agonists induce changes in receptors that place them in an active conformation that allows them to influence transcription, either positively or negatively. Most naturally produced ligands are agonists. However, synthetic hormone analogs may have more potent activity than the natural hormone. Examples include the synthetic glucocorticoids such as prednisone, dexamethasone, and triamcinolone that are used, e.g., to suppress inflammatory and immunologic responses.

On the other hand, an antagonist binds a receptor, but does not transmit a response. For example, antagonists bind to receptors, but fail to induce conformational changes that alter the receptor's transcriptional regulatory properties or physiologically relevant conformations. Binding of an antagonist can also block the binding and therefore the actions of an agonist. The antagonist usually competes for agonist binding and thereby prevents agonist actions. The body produces antagonists, but these usually circulate at levels too low to be effective. For example, progesterone can act as a mineralocorticoid or glucocorticoid receptor antagonist, but it interacts with both receptors with low affinity. Normal progesterone concentrations are too low for the steroid to occupy substantial numbers of either receptor. In contrast, synthetic hormone antagonists are clinically useful. Examples include the antistrogens tamoxifen and raloxxifene and the antiprogesetin and antiglucocorticoid, RU486.

Partial agonists or partial antagonists bind to receptors and yield a response less than that of a full agonist at saturating ligand concentrations. A partial agonist will block binding of a full agonist and suppress receptor activity to the level induced by the partial agonist alone. For example, partial agonists bind to receptors and induce only part of the changes in the receptors that are induced by agonists. The differences can be qualitative or quantitative. Thus, a partial agonist can induce some of the conformation changes induced by agonists, but not others, or it may only induce certain changes to a limited extent. Some of these compounds are naturally produced. For example, many plant estrogens (phytoestrogens), such as genistein, can behave as partial estrogen receptor agonists.

Mixed agonists-antagonists act in different ways through the same receptor type depending on context (which cells, which promoter, etc.). As an example, the estrogen "antagonists" tamoxifen and raloxifene act mostly as antagonists in breast but have estrogen agonist actions in bone and uterus.

Inverse agonists refer to ligands that exert agonist effects that are completely distinct from that of the native ligand. An example is that when estradiol binds to the β-form of its receptor there is little or no effect at genes with AP-1 sites, whereas tamoxifen and raloxifene show potent stimulatory effects at these sites.

While the present invention relates to agonists, the methods and composition of the invention can be modified to include the other types of ligands described above.

Discussion

Nuclear receptors utilize a discrete carboxy-terminal ligand-binding domain (LBD) that binds ligand and transduces this ligand binding signal into the appropriate biological response. X-ray structural analysis of nuclear receptor LBDs reveal a protein molecule composed of three layers of alpha helices in which the ligand is buried within the receptor's hydrophobic core. Structural and computer analyses of the ligand and receptor can help assess fit between the ligand and the pocket; the particular amino acids that line the pocket and the characteristics of their side chains. This information, in turn, guides the design of specific ligands that bind in the pocket. By adding chemical bulk in positions that clash with the receptor, it is possible to design compounds that disrupt the overall folding of the receptor and that influence its interactions with target cofactor proteins. However, the utility of this method of ligand design is limited by the fixed size and composition of the hormone-binding pocket. For example, it is desirable to obtain thyroid receptor (TR) isoform-specific ligands because these can have useful properties in reducing body weight and hypercholesterolemia (β-agonists) or in counteracting heart arrhythmias (α-antagonists). However, the hormone binding pockets of both thyroid hormone receptor isoforms only differ by a single amino acid, limiting the structure based approaches that can be used to generate isoform-specific binding. The present invention overcomes this limitation by providing agonist ligands comprising extensions that interact with regions of nuclear receptors outside of the ligand binding pocket. Because these agonists interact with additional residues on the nuclear receptors, there is additional opportunity for specific agonist-receptor interaction.

Nuclear Receptors

The invention can be used to produce, identify, design, etc., agonists for a variety of nuclear receptors, such as receptors for glucocorticoids (GRs), androgens (ARs), mineralocorticoids (MRs), progestins (PRs), estrogens (ERs), thyroid hormones (TRs), vitamin D (VDRs), retinoid (RARs and RXRs), and peroxisome proliferator activated receptors (PPARs)). For example, a nuclear receptor includes a thyroid hormone receptor, a β thyroid hormone receptor, an alpha thyroid hormone receptor, a glucocorticoid receptor, an estrogen receptor, an androgen receptor, a mineralocorticoid receptor, a progestin receptor, a vitamin D receptor, a retinoid receptor, a retinoid X receptor, a peroxisomal proliferator activated receptor, an estrogen-receptor related receptor, a short heterodimer partner, a constitutive androstane receptor, a liver X receptor, a pregnane X receptor, a HNF-4 receptor, a farnesoid X receptor (FXR) and an orphan receptor. Nuclear receptors can include nuclear receptors expressed by human and non-human species including vertebrates and invertebrates. A database of nuclear receptors is available on the World Wide Web at receptors.ucsf.edu/NR/multali/multali.html.

The invention can also be applied to "orphan receptors," that are structurally homologous in terms of modular domains and primary structure to classic nuclear receptors, such as steroid and thyroid receptors, e.g., a liver orphan receptor (LXR), a farnesoid X receptor (FXR), etc. The amino acid homologies of orphan receptors with other nuclear receptors range from very low (<15%) to in the range of 35% when compared to rat RAR-α and human TR-β receptors, for example. In addition, as is revealed by the X-ray crystallographic structure of the TR and structural analysis, the overall folding of liganded superfamily members is similar. See, U.S. Pat. No. 6,236,946 to Scanlan et al. entitled "Nuclear Receptor Ligands and Ligand Binding Domains" issued May 22, 2001; and, U.S. Pat. No. 6,266,622 to Scanlan et al., entitled "Nuclear Receptor Ligand Binding Domains" issued Jul. 24, 2001. Although ligands have not been identified with orphan receptors, once such ligands are identified, one skilled in the art will be able to apply the invention to the production, to the identification, to the designing, etc, of modified agonist ligands comprising extensions to these receptors, as these receptor's overall structural modular motif is similar to other nuclear receptors.

Isoforms

In one important aspect, the invention is applicable to generating agonists that display differential activity on nuclear receptor isoforms. That is, the extension on the ligand of interest can increase specificity as well as affinity—including specificity to distinguish between different forms of a given receptor. The term isoform refers to closely related receptors that can be products of distinct genes or products of differential splicing from the same gene. In general, isoforms encode receptors that would be assigned to the same class, e.g., for TR $\alpha 1$, $\alpha 2$, $\beta 1$, $\beta 2$, for PPAR $\alpha$, $\beta$, $\gamma$, for ER, $\alpha$ and $\beta$, in humans and the ERs $\alpha$ and $\beta$ and gamma in fish. The isoforms often bind the same ligand, but can also differ in their affinity of binding to particular ligands. It is desirable to design ligands that bind to and act selectively through one isoform.

As described herein, agonists of the invention can be generated that distinguish between different receptors or different isoforms of a given receptor, thereby allowing the generation of, e.g., tissue specific or function specific agonists (or both). For instance, GR subfamily members usually comprise one receptor encoded by a single gene, although are certain exceptions. For example, there are two PR isoforms, A and B, translated from the same mRNA by alternate initiation from different AUG codons. There are two GR forms, one of which does not bind ligand. In another example, the TR subfamily has several receptors that are encoded by at least two (TR: $\alpha$, $\beta$) or three (RAR, RXR, and PPAR: $\alpha$, $\beta$, $\gamma$) genes and/or that arise due to alternate RNA splicing. See, Yen (2001), above, for a review of TR receptor isoforms.

In one aspect, the invention includes methods for producing, identifying, designing, etc. a compound having agonist activity on a nuclear receptor, e.g., in an isoform-specific manner, e.g., on thyroid hormone receptor (TR). A "TR isoform" includes TR proteins encoded by subtype and variant TR genes. This includes TR-$\alpha$ and TR-$\beta$ isoforms encoded by different genes (e.g., TR$\alpha$ and TR$\beta$) and variants of the same genes (e.g., TR$\beta 1$ and TR$\beta 2$). One example use for agonists that are specific to one isoform over another is to provide agonists that reduce hypercholesterolemia (largely mediated by TR$\beta$) that do not affect the heart rate mediated mostly by TR$\alpha$.

Receptor Domain Organization

As already noted, nuclear hormone receptors have similar domain organization. The receptors are organized with an amino terminal A/B domain (sometimes referred to as a variable amino-terminal domain), a highly conserved central DNA binding domain comprising two zinc fingers (DBD) and a hinge region and a carboxy-terminal ligand binding domain (LBD). Details on the organizational structure of nuclear hormone receptors such as the thyroid receptor are found in Yen (2001), above. Gene sequences of representative nuclear receptors or their ligand binding domains have been cloned and sequenced, including the human RAR-alpha, human RAR-gamma, human RXR-alpha, human RXR-beta, human PPAR-alpha, human PPAR-beta, human PPAR-gamma, human VDR, human ER (as described in Seielstad et al., (1995) *Molecular Endocrinology*, 9:647-658), human TR-$\alpha$, human TR-$\beta$, human GR, human PR, human MR, and human AR, as well as mouse and/or rat or other homologues for many of these. The ligand binding domain of each of these nuclear receptors has been identified.

The LBD is the second most highly conserved domain in these receptors. While integrity of several different LBD sub-domains is important for ligand binding, truncated molecules containing only the LBD retain normal ligand-binding activity. This domain also participates in other functions, including dimerization, nuclear translocation and transcriptional activation and repression. This domain binds the ligand and undergoes ligand-induced conformational changes. See, e.g., U.S. Pat. No. 6,236,946 to Scanlan et al., entitled "Nuclear Receptor Ligands and Ligand Binding Domains" issued May 22, 2001; and, U.S. Pat. No. 6,266,622 to Scanlan et al., entitled "Nuclear Receptor Ligand Binding Domains" issued Jul. 24, 2001.

The LBD is necessary for hormone binding and also plays an important role in basal repression by unliganded receptor, as well as dimerization, and transactivation. The crystal structure of liganded thyroid receptor provides precise information as to ligand binding and function. See, Yen (2001), above; Bourguet et al. (1995) "*Crystal Structure of the ligand binding domain of the human nuclear receptor RXR-alpha*" Nature 375:377-382; Renaud et al. (1995) "*Crystal Structure of the RAR-gamma ligand binding domain bound to all-trans retinoic acid*"; Nature 378:681-689; Wagner et al. (1995) "*A structural Role for hormone in the thyroid hormone receptor*" Nature 378:690-697; Brzozowski et al. (1994) "*Molecular Basis of Antagonism in the Oestrogen Receptor*" Nature 389:753-758; Darimont et al. (1998) "*Structure and Specificity of Nuclear Receptor-Coactivator Interactions.*" Genes Dev 12:3343-3356; Feng et al. (1998) "*Hormone Dependent Coactivator Binding to a Hydrophobic Cleft on Nuclear Receptors*" Science 280:1747-1749; U.S. Pat. No. 6,266,622 (2001) "*Nuclear Receptor Ligands and Ligand Binding Domains*" by Scanlan et al.; and, Marimuthu et al (2002) "*Thyroid Hormone Receptor Surfaces and Conformations Required to Bind Nuclear Receptor Corepressor (N-CoR)*" Mol Endocrinol 16:271-86 (2002).

In the ligand binding domain, ligand is buried within a mostly hydrophobic pocket in the LBD formed by discontinuous stretches spanning the LBD. The most carboxy-terminal region (Helix 12) contributes its hydrophobic surface as part of the ligand binding pocket. The hydrophobic residues face inwards, whereas conserved glutamate residues of the helix face outwards. The pocket is bounded by hydrophobic surfaces from helixes 3, 4, and 5. The crystal structure of the unliganded RXR receptor shows that helix 12 projects into the solvent closing in "mouse trap" fashion on the ligand once bound. Helix 12 of raloxifene-bound ER LBD is in a different position, lying in a groove between helices 3 and 5. Thus, the relative positions of helix 12 and the boundary helixes determine whether coactivators can interact with a given receptor. FIG. 1 schematically shows the structure of thyroid receptor alpha binding its natural cognate ligand in the ligand binding pocket.

In the present invention, it was surprisingly discovered that extensions on various ligands can project out of the binding pocket, without disrupting coactivator binding surfaces on the receptor. Moreover, this extension provides additional specificity to ligand binding. That is, because ligand comprising an extension contacts additional receptor residues outside of the binding pocket, as compared to an unextended ligand. For example, in the case of GC-24, described above, the addition of a benzyl extension increases the specificity of the receptor for it Most members of the superfamily, including orphan receptors, possess at least two transcription activation sub-domains, one of which is constitutive and resides in the amino terminal domain (AF-1), and the other of which (AF-2 (also referenced as TAU 4)) resides in the ligand-binding domain whose activity is regulated by binding of an agonist ligand. Although the activity of AF-1 is not directly activated by ligand binding, it can be activated indirectly. For example, unliganded steroid hormone receptors are bound by heat shock proteins and rendered largely inactive. Binding of an agonist or in some cases antagonist ligand can cause dissociation of the heat shock protein with subsequent binding of the receptor to proteins or DNA where the AF-1 function can be active. The function of AF-2 requires an activation domain (also called transactivation domain) that is highly conserved among the receptor superfamily. Most LBDs contain this activation domain. Some mutations in this domain abolish AF-2 function, but leave ligand binding and other functions unaffected. Ligand binding allows the activation domain to serve as an interaction site for essential co-activator proteins that function to stimulate (or in some cases, inhibit) transcription. Based upon the structure of TRs, the activation domain is proposed to adopt an amphipathic helical structure. β-sheet or mixed secondary structures, can be present as activation domains in less related nuclear receptors.

Within the activation domain, the highly conserved motif ΦΦXEΦΦ, where Φ represents a hydrophobic residue, mediates interactions between the receptors and transcriptional coactivators. Several proteins have been identified which bind the TR in a hormone-dependent fashion. One of these, Trip1, is related to a putative yeast coactivator Sug1, and also interacts with both the C-terminal activation domain and a subset of the basal transcriptional machinery, suggesting a role in transactivation by the TR. Other proteins, such as RIP140, SRC1, (Onate, S. A. et. al., *Science* 270:1354-1357 (1995)) and TF-1 (see also Ledouarim, B., et. al., *EMBO J.* 14:2020-2033 (1995)), GRIP-1 (Heery, E., et al., *Nature* 387:733-736 (1997)) and TRAP220 (Fondell, J. D., Ge, H., and Roeder, R. G. (1996) *Proc Natl Acad Sci USA* 93:8329-8333) also interact with other nuclear receptors in a ligand dependent manner through the C-terminal domain. Binding of these proteins can be modulated using the agonists of the invention described herein with extensions that don't substantially disrupt the interaction between the highly conserved motif and other proteins.

The role of co-activators and co-repressors in steroid/thyroid hormone receptor systems is well known. See, for example, Shibata et al. (1997) *Recent Progress in Hormone Res.* 52:141-164 for a review. Steroid receptor co-activatorone (SRC-1) appears to be a general co-activator for all AF-2 domain containing receptors tested. SRC-1 enhances transactivation of hormone-dependent target genes. Other putative co-activators have been reported, including the SRC-1 related proteins, TIF-2 and GRIP-1 and pCIP/ACTR/AIB1, and other putative unrelated co-activators such as TRAP220, ARA-70, Trip 1, PGC-1. and TIF-1. In addition, another co-activator CREB-binding protein (CBP) has been shown to enhance receptor-dependent target gene transcription. CBP and SRC-1 interact and synergistically enhance transcriptional activation by the ER and PR. A ternary complex of CBP, SRC-1, and liganded receptors may form to increase the rate of hormone-responsive gene transcription. Co-repressors, such as SMRT and N-CoR, for TR and RAR, have been identified that also contribute to the silencing function of unliganded TR. The unliganded TR and RAR have been shown to inhibit basal promoter activity; silencing of target gene transcription by unliganded receptors is mediated by these co-repressors. It should be noted that coactivators such as GRIP1 can mediate negative effects on agonist bound nuclear receptors upon negatively regulated genes and co-repressors can mediate positive effects of unliganded receptors on negatively regulated genes.

The collective data show that upon binding of agonist, the receptor changes its conformation that enables recruitment of co-activators such as SRC-1, which allows the receptor to modify chromatin and interact with the basal transcriptional machinery more efficiently and to activate or repress transcription. In contrast, binding of antagonists induces either no or a different conformational change in the receptor. Although some antagonist-bound receptors can dimerize and bind to their cognate DNA elements, they typically fail to dislodge the associated co-repressors, which results in a nonproductive interaction with the basal transcriptional machinery. Similarly, TR and RAR associate with co-repressors in the absence of ligand, thereby resulting in a negative interaction with the transcriptional machinery that silences target gene expression. In the case of mixed agonist/antagonists, such as 4-hydroxytamoxifen, activation of gene transcription may depend on the relative ratio of co-activators and co-repressors in the cell or cell-specific factors that determine the relative agonistic or antagonistic potential of different compounds. These co-activators and co-repressors act as an accelerator and/or a brake that modulates transcriptional regulation of hormone-responsive target gene expression.

The carboxy-terminal activation subdomain, is in close three dimensional proximity in the LBD to the ligand, so as to allow for ligands bound to the LBD to coordinate (or interact) with amino acid(s) in the activation subdomain. As described herein, the LBD of a nuclear receptor can be expressed, crystallized, its three dimensional structure determined with a ligand bound (either using crystal data from the same receptor or a different receptor or a combination thereof), and computational methods used to design ligands to its LBD, including agonist ligands that contain an extension moiety that coordinates formation of the activation domain of the nuclear receptor.

The amino terminal domain is the least conserved of the three domains and varies markedly in size among nuclear receptor superfamily members. For example, this domain contains 24 amino acids in the VDR and 603 amino acids in the MR. This domain is involved in transcriptional activation and in some cases its uniqueness can dictate selective receptor-DNA binding and activation of target genes by specific receptor isoforms. This domain can display synergistic and antagonistic interactions with the domains of the LBD. For example, studies with mutated and/or deleted receptors show positive cooperativity of the amino and carboxy terminal domains. In some cases, deletion of either of these domains will abolish the receptor's transcriptional activation functions.

The DBD is the most conserved structure in the nuclear receptor superfamily. It usually contains about 70 amino acids that fold into two zinc finger motifs, wherein a zinc ion coordinates four cysteines. DBDs contain two perpendicularly oriented α-helixes that extend from the base of the first and second zinc fingers. The two zinc fingers function in concert along with non-zinc finger residues to direct nuclear receptors to specific target sites on DNA and to align receptor homodimer or heterodimer interfaces. Various amino acids in DBD influence spacing between two half-sites (usually comprised of six nucleotides) for receptor dimer binding. For example, GR subfamily and ER homodimers bind to half-sites spaced by three nucleotides and oriented as palindromes. The optimal spacings facilitate cooperative interactions between DBDs, and D box residues are part of the dimerization interface. Other regions of the DBD facilitate DNA-protein and protein-protein interactions required for RXR homodimerization and heterodimerization on direct repeat elements.

The LBD can influence the DNA binding of the DBD, and the influence can also be regulated by ligand binding. For example, TR ligand binding influences the degree to which a TR binds to DNA as a monomer or dimer. Such dimerization also depends on the spacing and orientation of the DNA half sites. The receptors also can interact with other proteins and function to regulate gene expression.

The nuclear receptor superfamily has been subdivided into two subfamilies: 1) GR (GR, AR, MR and PR) and 2) TR (TR, VDR, RAR, RXR, and most orphan receptors) on the basis of DBD structures, interactions with heat shock proteins (hsp), and ability to form heterodimers. GR subgroup members are tightly bound by hsp in the absence of ligand, dimerize following ligand binding and dissociation of hsp, and show homology in the DNA half sites to which they bind. These half sites also tend to be arranged as palindromes. TR subgroup members tend to be bound to DNA or other chromatin molecules when unliganded, can bind to DNA as monomers and dimers, but tend to form heterodimers, and bind DNA elements with a variety of orientations and spacings of the half sites, and also show homology with respect to the nucleotide sequences of the half sites. By this classification, ER does not belong to either subfamily, since it resembles the GR subfamily in hsp interactions, and the TR subfamily in nuclear localization and DNA-binding properties.

EXAMPLE

Agonist GC-24 for β Thyroid Receptor

This example shows a surprising and previously unexpected way of expanding the number of receptor residues in contact with a ligand, while preserving receptor function. This dramatically increases the potential for selective ligand design for nuclear receptors.

In this example, the properties of a new TR interacting ligand (GC-24) were determined. This ligand is based upon the chemical scaffold of GC-1, but contains a benzyl extension at the 3' position of the aryl ring. See, above. GC-24 showed a high degree of affinity and specificity for the TRβ isoform and functioned as an agonist to the receptor. Analysis of GC-24 interactions with mutated versions of TRβ and α indicated that this specificity does not solely arise from differences between the conventional ligand binding pockets, and must, therefore, derive from additional and previously unexpected determinants elsewhere in the molecule. We solved the crystal structure of GC-24 in complex with TRβ to understand this phenomenon. For example, see the atomic coordinates in Appendix I: Table 2. The crystal structure reveals that the GC-1 moiety of GC-24 is docked in the expected position within the ligand binding pocket, but the extension at the 3'-position is not in this pocket, but instead is inserted between the lower parts of helices 3 and 11 that become distorted, bending outward at their N and C termini, respectively, to accommodate the benzyl extension. Thus, the extra specificity of GC-24 arises from adventitious contacts between the benzyl extension and the new ligand-binding interface between helices 3 and 11. Even though parts of helices 3 and 11 are significantly distorted, the coactivator binding surface of the TR, formed by helices 3, 4, 5, 6 and 12 appears normal and GC-24 functions as a complete agonist in vivo and in vitro. Thus, the new ligand (GC-24) expands the ligand-binding pocket without adversely affecting receptor function.

Figure 2:
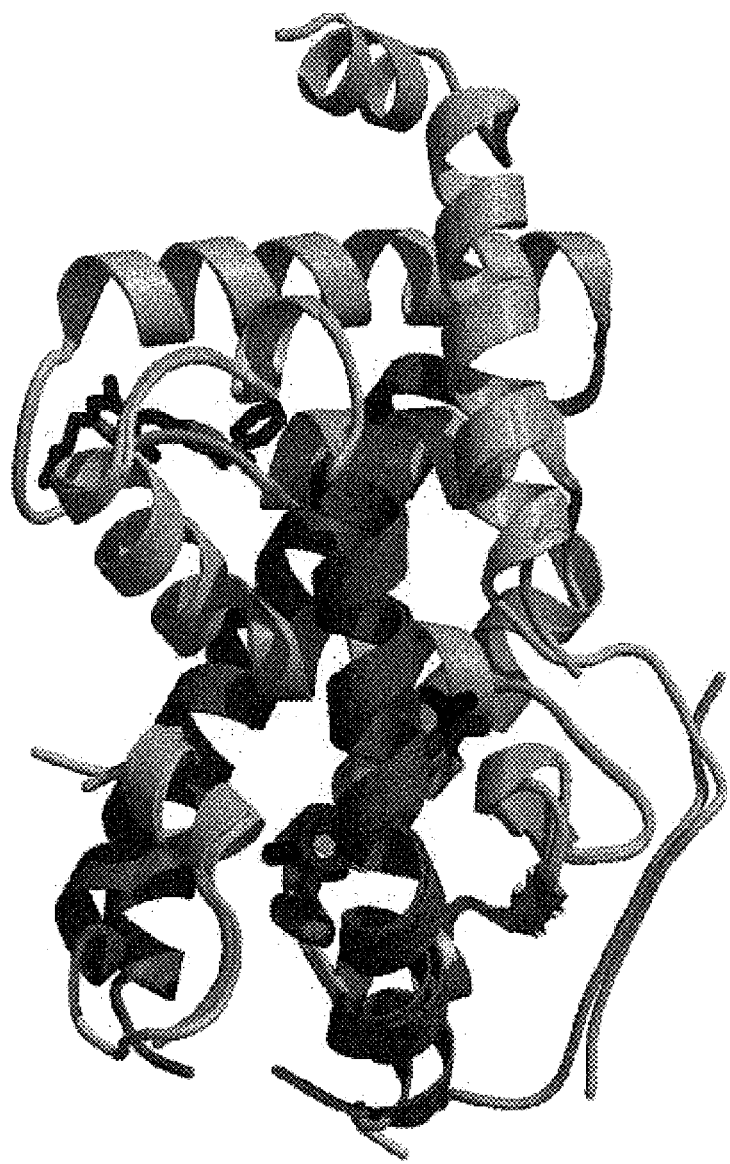
FIG. 2 schematically illustrates a comparison of TRβ/GC-24 complex versus TRβ/GC-1 complex, where helix 2 and 11 are moved. Orange shows GC-24 bound, while blue shows GC-1 bound.
Figure 3:
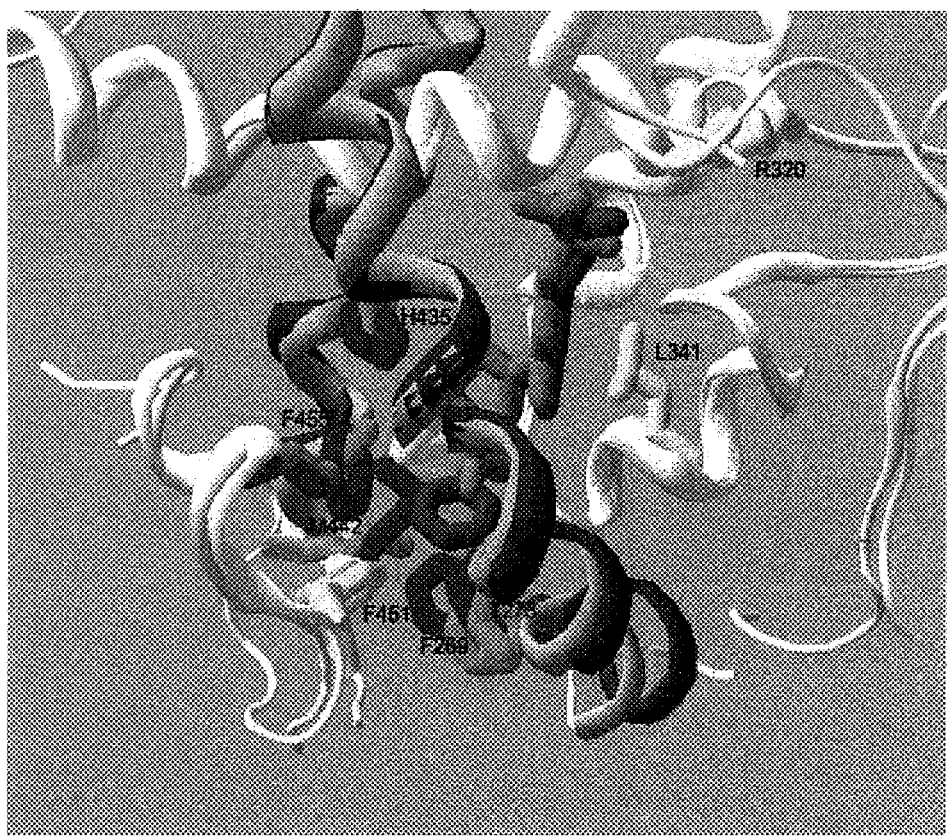
FIG. 3 schematically illustrates the changes in the positions of amino acids in TRβ binding GC-24. GC-24, in brown, changes the positions of amino acids F269, T273 (helix 3), H435, M442 (helix 11), and F455 (helix 12). These residues are shown in orange for GC-24 bound verses purple when GC-1 (light brown) is complexed with the receptor. R320, L341 and F451 (yellow) are neighbors within 4 Å in the GC-24 complex, but not when the ligand GC-1 is bound. Helix 3 and helix 11 are colored in dark gray.
Figure 4:
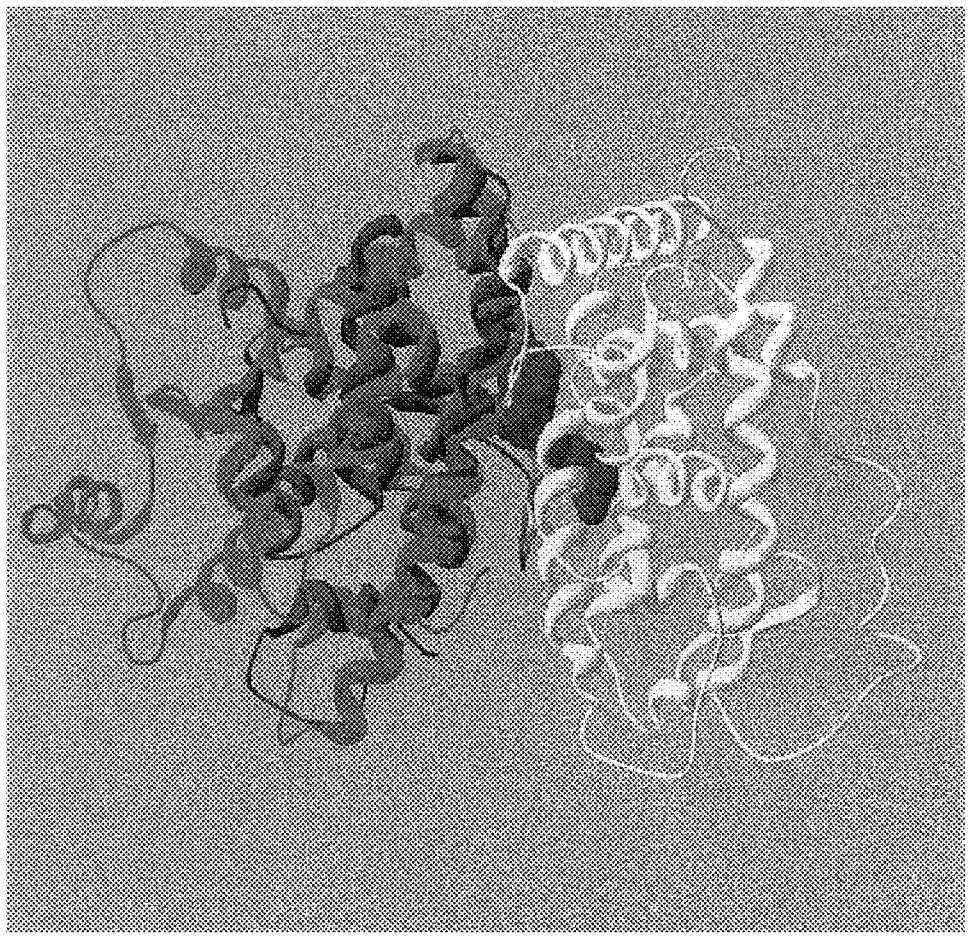
FIG. 4 schematically illustrates GC-24 at the interface of an RXR-heterodimer.
Figure 5:
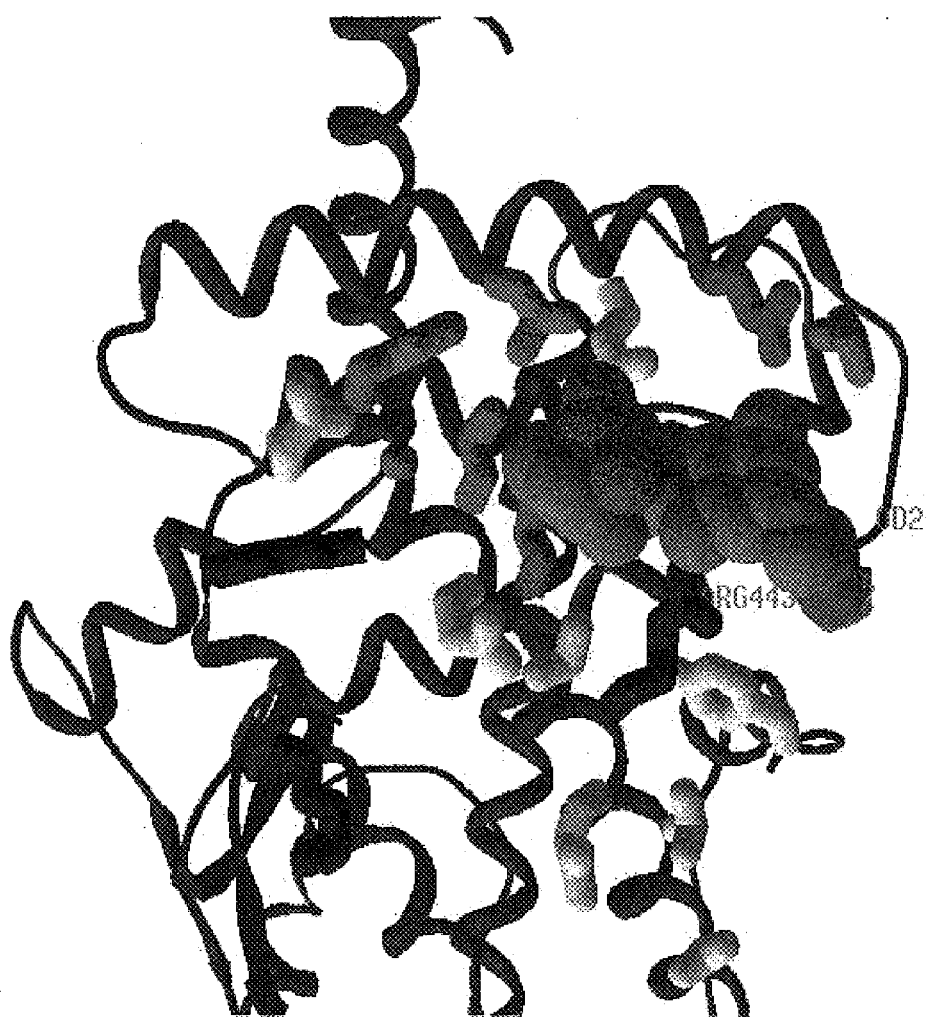
FIG. 5 schematically illustrates GC-24 at a nuclear receptor dimer regulatory site.

FIGS. 2-5 show binding of GC-24 to TR. FIG. 2 shows a comparison of binding of GC-24 and GC-1, demonstrating that Helix 3 and 11 are moved by binding of GC-24, as compared to binding of GC-1. FIG. 3 shows that the hormone-analog GC-24 (depicted in brown) changes the positions of amino acids F269, T273 (helix3), H435, M442 (helix11), and F455 (helix12). These residues are shown in orange for GC-24 bound vs. purple when GC-1 (light brown) is complexed with the receptor. R320, L341 and F451 (yellow) are neighbors within 4 Å in the GC-24 complex, but not when the ligand GC-1 is bound. Helix 3 and helix 11 are colored in dark gray. FIG. 4 shows the hormone analogue GC-24 at the interface of an RXR-Heterodimer. FIG. 5 shows GC-24 at a Nuclear Receptor dimer regulatory site.

The overall fold of the LBD is highly conserved between different members, of the nuclear receptor family, so this approach can be used to design new ligands for nuclear receptors generally. For example, these ligands contain extensions at a position that allows them to insert between helices 3 and 11, or at any point in the folded receptor structure that can accommodate a modest shift in helical position (e.g., without disrupting the cofactor binding surface). These shifts can be calculated using molecular modeling approaches to predict helix restructuring. In general, ligands are designed to bind to their receptors with high affinity by making some or all of the usual contacts with the conventional ligand binding pocket, coupled with additional contacts between the extension and new interfaces of the receptor. While this example highlights a way to make receptor-specific agonists, highly specific antagonists or mixed agonist/antagonists can be synthesized using the same principles. For example, an agonist with a large extension that exploits new receptor interfaces would be first identified. This new agonist ligand, with improved affinity or receptor subtype specificity, would then form the scaffold for new extensions that might perturb the coactivator binding pocket or any other functionally important region of the receptors.

Figure 6:
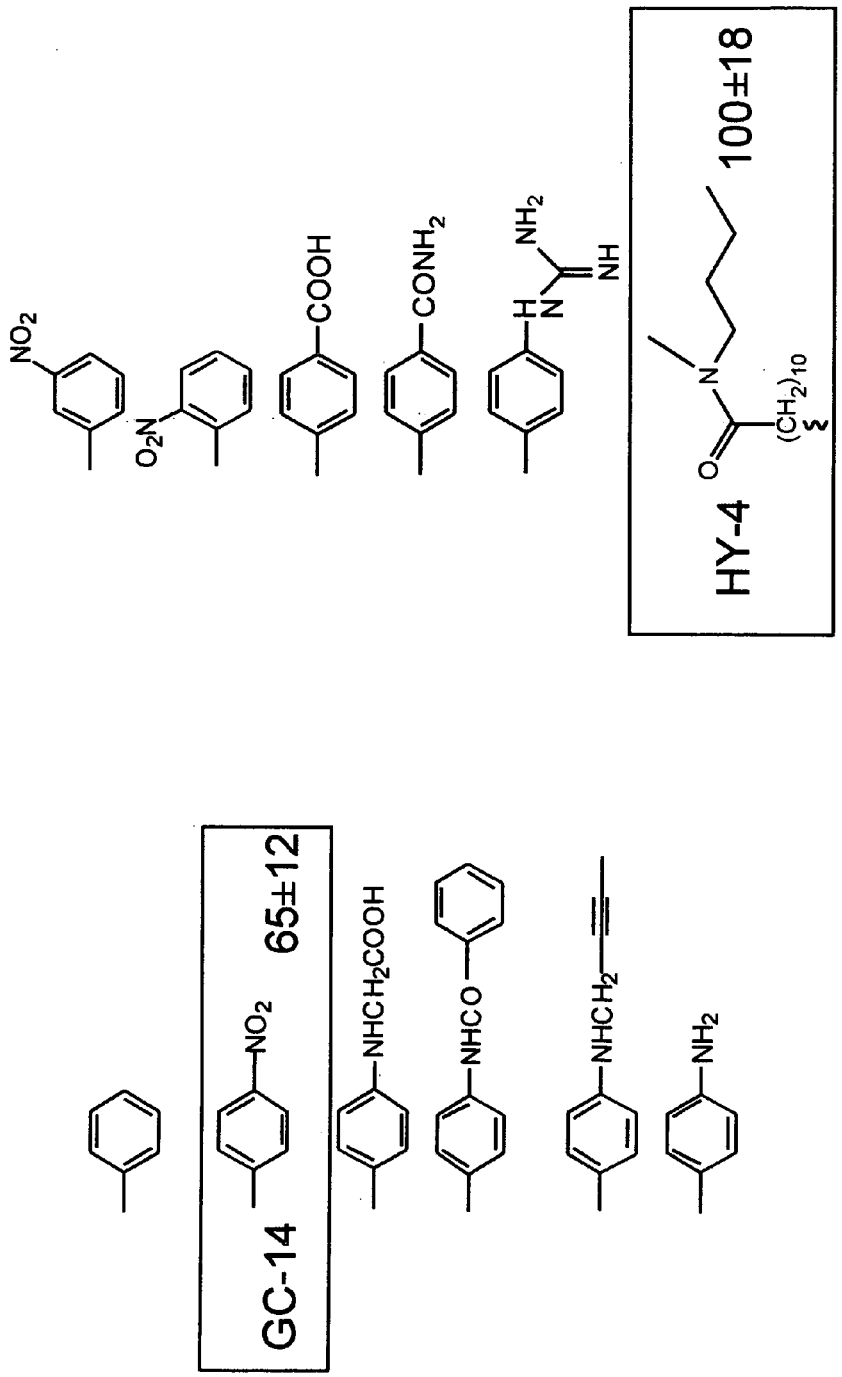
FIG. 6 displays 5'-aryl (GC series) or methylene bridge (HY-4) substituted GC-1 analogues.

This example also suggests a simple way to identify ligand compounds that comprise extensions, e.g., that will fit outside the ligand binding pocket. We synthesized a number of analogues of GC-1 that contained sizeable extensions (see e.g., FIG. 6) on the initial theory that these compounds would bind in the ligand-binding pocket, but would perturb the folding, resulting in an antagonist. Surprisingly, most compounds, as with GC-24, were found to be agonists, for the same basic reason as discussed above. Thus, a method provided by the invention is to screen compounds containing extensions for receptor binding and agonist activity. Such compounds are available and possess the requisite properties of an increased contact surface with the receptor. Variations of these molecules can be synthesized with or without performing determinations of the three-dimensional structures of the compound complexed with the receptor to yield improved molecules that could be tested in the same way.

It is emphasized that by forming an additional contact surface with additional residues for contact, the ligand is more likely to be more specific in its binding to that receptor vs. either other receptors or isoforms of the same receptor. The bulky side group decreases unwanted cross-reactive binding to other receptors.

Agonists of the Invention

An agonist of the invention optionally comprises the same or structurally similar groups of a naturally occurring hormone ligand while incorporating one or more extensions that result in the molecule having agonist activity. Alternatively, an agonist of the invention can be a molecule with little or no apparent structural similarity to the native ligand. However, in either case, the agonist will have a region that fits within the ligand binding pocket with some flexibility, interacting with the residues of the pocket, and an extension region that contacts the receptor in a region outside of the pocket. Typically, the extension enhances the normal operation of the ligand-nuclear receptor complex and/or generates the desired binding affinity or specificity through the interaction of the one or more extension with one or more receptor domains outside the ligand binding pocket. In one embodiment of the invention, when a nuclear receptor is bound to an agonist of the invention, the agonist comprises an increased specificity and/or affinity to the nuclear receptor compared to a naturally occurring ligand of the nuclear receptor. These properties, along with others, can be measured by, e.g., standard binding procedures, calculating or testing binding energies, computationally or using thermodynamic or kinetic methods as known in the art.

Extension

A ligand extension contacts a region of the nuclear receptor outside the native ligand binding pocket, e.g., a domain between helices, e.g., 3 and 11 or 3, 11 and 12, of the nuclear receptor. Optionally, the extension does not substantially disrupt the co-activator ligand binding surface, e.g., where the surface is formed by one or more of helices 3, 4, 5, 6 and 12 of the nuclear receptor. In one embodiment, the coactivator ligand binding surface comprises helices 3, 4, 5, 6 and 12. In one embodiment, the agonist of the invention can bind the receptor in the same basic orientation as the natural hormone, while the extension makes contacts with a region (e.g., space and/or amino acids) of the nuclear receptor that was not in contact with the ligand before the chemical modification was introduced. This, in turn, confers agonist activity on the receptor, as described herein.

The region can be determined by, e.g., the three dimensional structure of a nuclear receptor. See, the Nuclear Receptor section herein.

In one embodiment, the extension can be described by its size. For example, the extension can be, e.g., greater than about 50 Daltons and less than about 500 Daltons in size, greater than about 50 Daltons and less than about 300 Daltons in size, greater than about 75 Daltons and less than about 250 Daltons in size, etc. Similarly, the extension optionally includes, e.g., at least about carbons, at least about 5 carbons, at least about 6 carbons, at least about 7 carbons, at least about 8 carbons, at least about 9 carbons, at least about 10 carbons or more. The extension is large enough to extend through the ligand binding pocket, without disrupting formation of the co-activator surface.

In another embodiment, the extension comprises a —XR moiety, where the X is selected from the group consisting of: a $CH_2$, an O, a S, a NH, a NR", a CHR", and a $CR''_2$, and where R" is an H or a lower alkyl, and where R is selected from the group consisting of: a phenyl, a 5-member heterocyclic ring, a 6-member heterocyclic ring, a substituted phenyl, a substituted 5-member heterocyclic ring, and a substituted 6-member heterocyclic ring. In one embodiment, the extension is located at the $R_3$' position of the Formula I described below. For example, the extension is a benzyl moiety, e.g., at the $R_3$' position of Formula I described below.

For example, a general structure for one class of agonists of the invention is exemplified in the following general description of the substituents of a TR ligand of Formula 1:

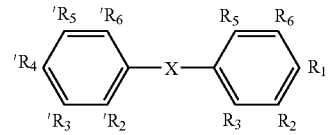

$R_1$ can have anionic groups such as a carboxylate, phosphonate, phosphate, sulfate or sulfite and is connected to the ring with a 0 to 3 atom linker, comprising: one or more C, O, N, S atoms, and preferably a 2 carbon linker. $R_1$ can be optionally substituted with an amine (e.g. —$NH_2$). $R_3$ and $R_5$ are small hydrophobic groups, such as —Br, —I, or —$CH_3$. $R_3$ and $R_5$ can be the same substituents or different. $R_3$' can be a hydrophobic group that can be larger than those of $R_3$ and $R_5$, such as —I, —$CH_3$, -isopropyl, —X'R moiety, where the X' is selected from the group consisting of a $CH_2$, an O, a S, a NH, a NR", a CHR", and a $CR''_2$ and where R" is an H or a lower alkyl, and where R is selected from the group consisting of a phenyl, a 5-member heterocyclic ring, a 6-member heterocyclic ring, a substituted phenyl, a substituted 5-member heterocyclic ring and a substituted 6-member heterocyclic ring. $R_4$' is a group that can participate in a hydrogen bond as either a donor or acceptor. Such groups include —OH, —$NH_2$, and —SH. $R_5$' can comprise an extension group that also can make this compound an agonist of the invention. See also, FIG. 6. $R_5$' can be a long chain alkyl (e.g. 1 to 9 carbons, straight chain or branched), aryl (benzyl, phenyl and substituted benzyl and phenyl rings (e.g. with halogen, alkyl (1 and 5 carbons) and optionally connected to the ring by a —$CH_2$—), heterocycle (e.g. 5 or 6 atoms, preferably 5 carbons and 1 nitrogen, or five carbons), which can optionally include polar (e.g. —OH, —$NH_2$, and —SH), cationic (e.g. —$NH_3$, $N(CH_3)_3$), or anionic (carboxylate, phosphonate, phosphate or sulfate) groups. $R_5$' can also be a polar (e.g. —OH, —$NH_2$, and —SH), cationic (e.g. —$NH_3$, —$N(CH_3)_3$), or anionic (carboxylate, phosphonate, phosphate or sulfate) group. X in Formula 1 is the spacer group that appropriately positions the two aromatic rings. This group is usually a one-atom spacer, such as O, S, SO, $SO_2$, NH, NZ where Z is an alkyl, $CH_2$, CHOH, CO, $C(CH_3)OH$, and $C(CH_3)(CH_3)$. X also can be $NR_7$, $CHR_7$, $CR_7$, $R_7$, is an alkyl, aryl or 5- or 6-membered heterocyclic aromatic. $R_2$, $R_6$, $R_2$' and $R_6$' can be —F, and/or —Cl and/or are preferably H.

A TR ligand can also be described as a substituted phenylated 3,5-diiodo tyrosine with substituted $R_5$' and $R_3$' groups. $R_5$' can be a long chain alkyl (e.g. 4 to 9 carbons, straight chain or branched), aryl (benzyl, phenyl and substituted benzyl and phenyl rings (e.g. with halogen, alkyl (1 and 5 carbons) and optionally connected to the ring by a —$CH_2$—), heterocycle (e.g. 5 or 6 atoms, preferably 5 carbons and 1 nitrogen, or five carbons), which can optionally include polar (e.g. —OH, —$NH_2$, and —SH), cationic (e.g. —$NH_3$, $N(CH_3)_3$), or anionic (carboxylate, phosphonate, phosphate or sulfate) groups. $R_5$' can also be a polar (e.g. —OH, —$NH_2$, and —SH), cationic (e.g. —$NH_3$, $N(CH_3)_3$), and anionic (carboxylate, phosphonate, phosphate or sulfate) groups. $R_3$' can be -IsoPr, halogen, —$CH_3$, alkyl (1 to 6 carbons) or aryl (benzyl, phenyl and substituted benzyl and phenyl rings (e.g. with halogen, alkyl (1 and 5 carbons)) which is optionally connected to the ring by a —X, where the X is selected from the group consisting of a $CH_2$, an O, a S, a NH, a NR", a CHR", and a $CR''_2$ and where R" is a H or a lower alkyl, or a heterocycle or substituted heterocycle (e.g. 5 or 6 atoms, preferably 5 carbons and 1 nitrogen, or five carbons), which can optionally include polar (e.g. —OH, —NH$_2$, and —SH), cationic (e.g. —NH$_3$, N(CH$_3$)$_3$), or anionic (carboxylate, phosphonate, phosphate or sulfate) groups) which is optionally connected to the ring by a —X, where the X is selected from the group consisting of a CH$_2$, an O, a S, a NH, a NR", a CHR", and a CR"$_2$ and where R" is a H or a lower alkyl.

A TR agonist can also be a modified T$_3$ agonist (having a biphenyl structure) wherein R$_5$' is alkyl, aryl, 5- or 6-membered heterocyclic aromatic, heteroalkyl, heteroaryl, arylalkyl, heteroaryl alkyl, polyaromatic, polyheteroaromatic, polar or charged groups, wherein said R$_5$' can be substituted with polar or charged groups. The R$_5$' groups are defined, as described herein.

The invention also includes means for contacting a region of the nuclear receptor outside the native ligand binding domain of the nuclear receptor. These means include those described herein. For example, means includes an extension, e.g., greater than about 50 Daltons and less than about 500 Daltons in size, greater than about 50 Daltons and less than about 300 Daltons in size, greater than about 75 Daltons and less than about 250 Daltons in size, etc. Means also includes an extension with carbons, e.g., at least 3 carbons, at least 5 carbons, at least 6 carbons, at least 7 carbons, at least 8 carbons, at least 9 carbons, at least 10 carbons or more. In another embodiment, the means includes a —XR moiety, where the X is selected from the group consisting of a CH$_2$, an O, a S, a NH, a NR", a CHR", and a CR"$_2$ and where R" is a H or a lower alkyl, and where R is selected from the group consisting of a phenyl, a 5-member heterocyclic ring, a 6-member heterocyclic ring, a substituted phenyl, a substituted 5-member heterocyclic ring and a substituted 6-member heterocyclic ring.

Nuclear Receptor Complexes

The invention provides for a nuclear receptor agonist complex, which includes a nuclear receptor bound to an agonist, where the agonist includes an extension, described herein, or means for contacting a region of the nuclear receptor outside of a native ligand binding pocket. For example, an agonist includes a molecule derived from chemical structure of GC-1 with an extension, e.g., a benzyl moiety. See, U.S. Pat. No. 6,266,622 to Scanlan et al., entitled "Nuclear Receptor Ligand Binding Domains" issued Jul. 24, 2001. In one embodiment, the extension is located at the 3' position of the aryl ring in the chemical structure of GC-1, e.g., GC-24.

Complexes of the invention can be formed or used in vitro or in vivo or a combination of both. For example, the complex can be in a container or alternatively a cell, or an organism, e.g., a mammal, such as a human. Optionally, the nuclear receptor is activated in the nuclear receptor agonist complex.

Libraries of agonists for a nuclear receptor are also included in the invention. See Libraries of Agonists section below.

Producing, Identifying and Designing Agonists

Method of producing, identifying and designing agonists for nuclear receptors are also provided. Methods for producing an agonist for a nuclear receptor include: providing a modified nuclear receptor ligand comprising an extension, where the extension contacts a region of the nuclear receptor outside of a native ligand binding pocket of the nuclear receptor; and, confirming that the modified nuclear receptor ligand comprises agonist activity on the nuclear receptor, thereby producing the agonist. In one embodiment, the confirming includes the steps of binding the modified nuclear receptor ligand to the nuclear receptor; and, testing the resulting ligand bound nuclear receptor for agonist activity. An agonist produced by the method is also provided in the invention. In one embodiment, the agonist is GC-24. Alternatively, the agonist is an agonist other than GC-24.

The invention also provides a method for producing an agonist of a nuclear receptor, where the method includes providing a modified nuclear receptor ligand comprising means for contacting a region of the nuclear receptor outside of a native ligand binding pocket of the nuclear receptor; and, confirming that the modified nuclear receptor ligand comprises agonist activity on the nuclear receptor, thereby producing the agonist.

Methods for identifying one or more agonists for a nuclear receptor include the steps of providing a plurality of putative agonists, each comprising an extension, where the extension contacts a region of the nuclear receptor outside of the native ligand binding pocket; and, testing the putative agonists for agonist activity on the nuclear receptor, thereby identifying the one or more agonists of the nuclear receptor. An agonist and/or a library that includes a plurality of different agonists produced by this method is also included in the invention.

Other methods for identifying one or more agonists for a nuclear receptor include providing a plurality of putative agonists, each comprising means for contacting a region of the nuclear receptor outside of the native ligand binding pocket; and, testing the putative agonists for agonist activity on the nuclear receptor, thereby identifying the one or more agonists of the nuclear receptor. In another embodiment, a nuclear hormone receptor agonist can also be identified by screening a putative nuclear hormone receptor antagonist, where the antagonist comprises an extension for agonist activity on the nuclear hormone receptor.

Providing Agonist

In one embodiment, providing the agonist includes synthesizing the modified nuclear receptor ligand or a plurality of putative agonists. For example, see U.S. Pat. No. 6,236, 946 to Scanlan et al. entitled "Nuclear Receptor Ligands and Ligand Binding Domains" issued May 22, 2001; and, U.S. Pat. No. 6,266,622 to Scanlan et al., entitled "Nuclear Receptor Ligand Binding Domains" issued Jul. 24, 2001. Providing the agonist can also include providing a nuclear receptor ligand, e.g., a native or non-native ligand, and modifying the ligand by coupling an extension to the receptor ligand. A plurality of, e.g., native ligands, nuclear receptor ligands can also be provided and modified by coupling a plurality of different extensions to the plurality of receptor ligands.

Designing Agonist

Putative agonists of nuclear receptor can also be designed. The overall folding of nuclear receptors based on a comparison of the reported structure of the unliganded RXR and with amino acid sequences of other superfamily members reveals that the overall folding of receptors of the superfamily is similar. It is predicted from the structure that there is a general pattern of folding of the nuclear receptor around the agonist ligand. Thus, by inspecting the three dimensional model of a protein or polypeptide that includes the nuclear receptor binding pocket, a putative agonist for the nuclear receptor can be designed. Steps include providing a three dimensional model of a protein or polypeptide that includes a nuclear receptor ligand binding pocket of the nuclear receptor of interest and modeling binding of one or more compounds to the three dimensional model. Each compound includes one or more extensions that spatially fit into a contact region outside the ligand binding pocket of the protein, e.g., formed by helices, e.g., 3 and 11 or 3, 11, and 12, of the nuclear receptor, and that do not substantially disrupt a coactivator binding surface of the receptor, e.g., formed by one or more of helices 3, 4, 5, 6 and 12 of the nuclear receptor. In one embodiment, the coactivator binding surface of the receptor is formed by helices 3, 4, 5, 6 and 12. Typically, the extension is added to selected positions on a naturally occurring or synthetic ligand. In one embodiment, the putative agonists can be tested for agonist activity as described herein and methods known on one of skill in the art.

By "modeling" is intended quantitative and qualitative analysis of receptor-ligand structure/function based on three-dimensional structural information and receptor-ligand interaction models. This includes conventional numeric-based molecular dynamic and energy minimization models, interactive computer graphic models, modified molecular mechanics models, distance geometry and other structure-based constraint models. Modeling is preferably performed using a computer and can be further optimized using known methods.

Computer programs that use crystallography data can be used to rationally design putative agonists of nuclear receptors. Programs such as RASMOL can be used with the atomic coordinates from crystals of nuclear receptors or nuclear receptor-ligand complexes by generating three dimensional models and/or determining the structures involved in ligand binding. Computer programs such as INSIGHT and GRASP allow for further manipulation and the ability to introduce new structures.

For example, a putative TR agonist ligand can be designed by providing the atomic coordinates of a TR LBD to a computerized modeling system, and modeling ligands which fit spatially into the TR LBD and that contact a region outside the native ligand binding pocket formed by the LBD and that do not substantially disrupt the co-activator binding surface. The putative agonists can then be identified in a biological assay for TR activity a ligand that increases the activity of the TR.

Confirming or Testing Agonist Activity

Once the modified nuclear receptor ligand, a putative agonist(s), or a plurality of putative agonists is provided, it can be confirmed or tested using assays to establish its activity as an agonist, specificity, and/or affinity, as described herein. Confirming or testing of agonist activity can be done in vitro or in vivo or a combination of both. In one embodiment, this includes binding a modified nuclear ligand to the nuclear receptor and testing the resulting ligand bound nuclear receptor for agonist activity. In another embodiment, testing includes binding a plurality of putative agonists to the nuclear receptor, selecting for members of the plurality of putative agonists that bind the nuclear receptor, and testing the resulting ligand bound nuclear receptors for agonist activity.

Agonist activity can be confirmed, or tested by a variety of methods known to one of skill in the art. For example, activation (and binding of an agonist) of the nuclear receptor can be determined by, e.g., alterations in transcription of at least one nuclear receptor responsive gene, dissociation of a heat shock protein from the nuclear receptor, dimerization of the nuclear receptor, dissociation of one or more transcriptional repressor proteins from the nuclear receptor, a conformation change in the receptor, etc. Suitable assays are described herein and in, e.g., Shibata, H., et al. (1997) *Recent Prog. Horm. Res.* 52:141-164; Tagami, T., et al. (1997) *Mol. Cell Biol.* 17(5):2642-2648; Zhu, X G., et al. (1997) *J. Biol. Chem.* 272(14):9048-9054; Lin, B. C., et al. (1997) *Mol. Cell Biol.* 17(10):6131-6138; Kakizawa, T., et al. (1997) *J. Biol. Chem.* 272(38):23799-23804; and, Chang, K. H., et al. (1997) *Proc. Natl. Acad. Sci. USA* 94(17):9040-9045. For example, high throughput binding and bioactivity assays can be devised using purified recombinant protein and modern reporter gene transcription assays described herein and known in the art in order to confirm, test, etc. for agonist activity. Agonists of the invention can affect one or more of these activities.

Alterations in transcription of a nuclear responsive gene can be used for assaying nuclear receptor activation. In nuclear receptors that bind to heat shock protein (hsp), the ligand-induced dissociation of hsp with consequent dimer formation allows, and therefore, promotes DNA binding. With receptors that are not associated with hsp (as in the absence of ligand), ligand binding can stimulate DNA binding of heterodimers and dimers, and discourage monomer binding to DNA. However, ligand binding to TR, for example, tends to decrease dimer binding on certain DNA elements and has minimal to no effect on increasing heterodimer binding. With DNA containing only a single half site, the ligand tends to stimulate the receptor's binding to DNA. The effects are modest and depend on the nature of the DNA site and probably on the presence of other proteins that may interact with the receptors. Nuclear receptors usually have DBDs that present a region for binding to DNA and this binding can be modulated by the binding of a ligand to the LBD. Consequently, an agonist of the invention will have the same properties to influence DNA binding in the manner described above. Typically, an extension contacts a region of the nuclear receptor outside of the native ligand binding pocket. Optionally, the extension fits into the region without substantially disrupting a coactivator ligand binding surface of the nuclear receptor.

Ligand binding induces transcriptional activation functions in two basic ways. The first is through dissociation of the hsp from receptors. This dissociation, with consequent dimerization of the receptors and their binding to DNA or other proteins in the nuclear chromatin allows transcriptional regulatory properties of the receptors to be manifest. This may be especially true of such functions on the amino terminus of the receptors.

The second way is to alter the receptor interaction with other proteins involved in transcription. These could be proteins that interact directly or indirectly with elements of the proximal promoter or proteins of the proximal promoter. Alternatively, the interactions could be through other transcription factors that themselves interact directly or indirectly with proteins of the proximal promoter. Several different proteins have been described that bind to the receptors in a ligand-dependent manner. In addition, it is possible that in some cases, the ligand-induced conformational changes do not affect the binding of other proteins to the receptor, but do affect their abilities to regulate transcription.

Nuclear receptors or nuclear receptor LBDs usually have activation domains modulated in part by a co-activator/co-repressor system that coordinately functions to present a region for binding to DNA, and that can be modulated by the binding of a ligand to the LBD. Consequently, an extension does not substantially disrupt the binding or contact of the activation domain with co-activator and/or co-repressor. For instance, an agonist can be designed, identified and/or produced which (1) blocks binding and/or dissociates co-repressor, and/or (2) promotes binding and/or association of a co-activator. An antagonist can be designed which (1) promotes binding and/or association of co-repressor, and/or (2) blocks binding and/or association of co-activator. Ratios of agonists and antagonists can be used to modulate transcription of the gene of interest.

Dissociation of a heat shock protein from the nuclear receptor can also be used for assaying for nuclear receptor activation. For many of the nuclear receptors ligand binding induces a dissociation of heat shock proteins such that the receptors can form dimers in most cases, after which the receptors bind to DNA and regulate transcription. Nuclear receptors usually have heat shock protein binding domains that present a region for binding to the LBD and can be modulated by the binding of a ligand to the LBD. Consequently, an agonist of the invention can destabilize the binding or contact of the heat shock protein binding domain with the LBD. Typically, an extension contacts a region of the nuclear receptor outside of the native ligand binding pocket. Optionally, the extension fits into the region without substantially disrupting a coactivator ligand binding surface of the nuclear receptor.

Dimerization or heterodimerization of the nuclear receptor can also be used to assay receptor activation. With the receptors that are associated with the hsp in the absence of the ligand, dissociation of the hsp results in dimerization of the receptors. Dimerization is due to receptor domains in both the DBD and the LBD. Although the main stimulus for dimerization is dissociation of the hsp, the ligand-induced conformational changes in the receptors can have an additional facilitative influence. With the receptors that are not associated with hsp in the absence of the ligand, particularly with the TR, ligand binding can affect the pattern of dimerization/heterodimerization. The influence depends on the DNA binding site context, and can also depend on the promoter context with respect to other proteins that may interact with the receptors. A common pattern is to discourage dimer formation, with a resulting preference for heterodimer formation over dimer formation on DNA.

Nuclear receptor LBDs usually have dimerization domains that present a region for binding to another nuclear receptor and can be modulated by binding of a ligand to the LBD. Consequently, an agonist of the invention will activate the binding or contact of the dimerization domain. Typically, an extension contacts a region of the nuclear receptor outside of the native ligand binding pocket. Optionally, the extension fits into the region without substantially disrupting a coactivator ligand binding surface of the nuclear receptor.

As mentioned above, dissociation of one or more transcriptional repressor proteins from the nuclear receptor can be assayed for receptor activation. Receptors that are not associated with hsp in the absence of ligand can act as transcriptional repressors of positively regulated genes in the absence of the ligand. This appears to be due, in part, to transcriptional repressor proteins that bind to the LBD of the receptors. Agonist binding induces a dissociation of these proteins from the receptors. This relieves the inhibition of transcription and allows the transcriptional transactivation functions of the receptors to become manifest. Unliganded receptors that are not associated with hsp can also activate gene transcription in some contexts. Here, ligand binding reverses the positive effect of unliganded receptor and suppress receptor activity below basal levels.

Activation of the nuclear receptor can also be confirmed or tested by using assays that examine ligand-induced conformational changes. Ligand binding by the receptor is a dynamic process, which regulates receptor function by inducing an altered conformation. The unliganded receptor is in a configuration that is either inactive, has some activity or has repressor activity. Binding of agonist ligands induces conformational changes in the receptor such that the receptor becomes more active, either to stimulate or repress the expression of genes. The receptors can also have non-genomic actions.

An unliganded receptor can be compared to a nuclear receptor with bound agonist using conventional techniques. For example, a column can be used that separates the receptor according to charge, such as an ion exchange or hydrophobic interaction column. The agonist induces a change in the receptor's surface charge such that the agonist-bound receptor elutes at a different position than the unbound receptor.

Various conformations of receptors can also be assessed by phage technology. With this technology, bacteriophage libraries that express random peptide sequences that are presented on the surface of the phage particle (Phage display) can be screened to isolate peptides that recognize individual conformational states of receptors. Thus, phage can be isolated that express peptides that distinguish between agonist and antagonist forms of the receptor, receptors in various states of transcriptional activation, and possibly between receptors whose extensions have inserted into the body or the receptor in various ways. Such phage can then be used to screen libraries of compounds for the requisite conformation. With respect to the current invention, this would be conformations that reflect the agonist state of the receptor or the state in which an extension is inserted outside the ligand binding pocket. See, e.g., Wijayaratne et al (1999) *Endocrinology.* 140:5828; Chang et al (1999) *Mol Cell Biol* 19:8226; Norris et al (1999) *Science* 285:744; and, Paige et al (1999) *PNAS* 96:3999.

After such confirmation or testing, the agonists of the invention can be further refined by generating full or partial nuclear receptor protein crystals with an agonist of the invention bound to the receptor. The structure of the agonist can then be further refined using chemical modification methods for three dimensional models to improve activity or affinity of the agonist and to make second generation agonists with improved properties.

Libraries of the Invention

The present invention provides a variety of libraries, including libraries of agonists, receptors and receptor/agonist complexes. For example, in one aspect, the invention provides libraries of agonists for a nuclear receptor, in which the library comprises a plurality of different agonists. More than one of the different agonists comprise a nuclear receptor ligand with an extension, which contacts a region of the nuclear receptor outside of a native ligand binding pocket.

Not all of the agonists in the library necessarily need to have an extension, i.e., mixed libraries comprising ligands with and without extensions can be made and screened in the assays of the invention. Typically, at least about 1% of the library members will comprise extensions. In certain embodiments, 10%, 20%, 50%, 80%, 90% or 95% or more of the library members will comprise an extension. The precise percentage can be selected by the user based, e.g., upon the intended use for the library.

Similarly, the library of agonists is optionally formatted in an arrangement of elements that comprises non-agonists (unrelated molecules, antagonists, or the like). The library of agonists is made up of the agonist members of the arrangement of elements, rather than the non-agonist elements. The overall arrangement of agonists and non-agonists can be referred to as a mixed element library.

The precise physical layout of the library is at the discretion of the practitioner. One can conveniently utilize gridded arrays of library members, e.g., formatted in a microtiter dish, or dried on a substrate such as a membrane, but other arrangements, are entirely appropriate, including those in which the library members are stored in separate locations that are accessed by one or more access control elements (e.g., that comprise a database of library member locations). The library format can be accessible by conventional robotics, or microfluidic devices, or a combination thereof.

One common array format for use is a microtiter plate array, in which the library comprises an array embodied in the wells of a microtiter tray (or the components therein). Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use.

In addition to libraries that comprise liquid phase arrays, agonist components can be stored in libraries comprising solid phase arrays of agonists. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. Components can be accessed, e.g., by local rehydration (e.g., using a pipette or other fluid handling element) and fluidic transfer, or by scraping the array or cutting out sites of interest from the array.

While component libraries are most often thought of as physical elements with a specified spatial-physical relationship, the present invention can also make use of "logical" libraries, which do not have a straightforward spatial organization. For example, a computer system can be used to track the location of one or several components of interest, which are located in or on physically disparate components. The computer system creates a logical library by providing a "look-up" table of the physical location of array members (e.g., using a commercially available inventory tracking system). Thus, even components in motion can be part of a logical library, as long as the members of the library can be specified and located.

The libraries of the invention optionally include any of the physical components of the invention described anywhere herein, including agonists (including agonists having any physical structure noted herein), agonist/receptor complexes (including those having any physical structure noted herein), or the like. Thus, the agonist can include any of the extension structures discussed herein (e.g., a —XR moiety, where the X is selected from the group consisting of a $CH_2$, an O, a S, a NH, a NR", a CHR", and a $CR"_2$ and where R" is a H or a lower alkyl, and where R is selected from the group consisting of a phenyl, a 5-member heterocyclic ring, a 6-member heterocyclic ring, a substituted phenyl, a substituted 5-member heterocyclic ring and a substituted 6-member heterocyclic ring), or a group having a given size (e.g., between 50 and 500 Da), or the like. Similarly, the receptor can be any of those noted herein, e.g., TR, GR, ER, etc. In preferred embodiments, members of the agonist library include extensions that spatially fit into the receptor without substantially disrupting a coactivator binding surface of the receptor.

Indeed, virtually any agent can be formatted into a library and screened as a putative agonist according to the methods of this invention. Such agents include, but are not limited to, small organic molecules, nucleic acids, proteins, sugars, polysaccharides, glycoproteins, lipids, and the like. The term "small organic molecules" typically refers to molecules of a size comparable to those organic molecules generally used as pharmaceuticals. The term excludes biological macromolecules (e.g., proteins, nucleic acids, etc.).

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic agonist activity. The compounds thus identified can serve as conventional "lead compound" or can themselves be used as agonists, including as potential or actual therapeutics.

A combinatorial chemical library is a collection of diverse compounds generated by chemical synthesis, or biological synthesis (or both), by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) *J. Med. Chem.*, 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487-493, Houghton et al. (1991) *Nature*, 354: 84-88); peptoids (PCT Publication No WO 91/19735, Dec. 26, 1991); encoded peptides (PCT Publication WO 93/20242, Oct. 14, 1993); random bio-oligomers (PCT Publication WO 92/00091, Jan. 9, 1992); benzodiazepines (U.S. Pat. No. 5,288,514); diversomers such as hydantoins, benzodiazepines and dipeptides (Hobbs et al., (1993) *Proc. Nat. Acad. Sci. USA* 90: 6909-6913); vinylogous polypeptides (Hagihara et al. (1992) *J. Amer. Chem. Soc.* 114: 6568); nonpeptidal peptidomimetics with a Beta-D-Glucose scaffolding (Hirschmann et al., (1992) *J. Amer. Chem. Soc.* 114: 9217-9218); analogous organic syntheses of small compound libraries (Chen et al. (1994) *J. Amer. Chem. Soc.* 116: 2661); oligocarbamates (Cho, et al., (1993) *Science* 261:1303), peptidyl phosphonates (Campbell et al., (1994) *J. Org. Chem.* 59: 658); Gordon et al., (1994) *J. Med. Chem.* 37:1385, nucleic acid libraries (see, e.g., Strategene, Corp.); peptide nucleic acid libraries (see, e.g., U.S. Pat. No. 5,539,083); antibody libraries (see, e.g., Vaughn et al. (1996) *Nature Biotechnology*, 14(3): 309-314), and PCT/US96/10287); carbohydrate libraries (see, e.g., Liang et al. (1996) *Science*, 274: 1520-1522, and U.S. Pat. No. 5,593,853), and small organic molecule libraries (see, e.g., benzodiazepines, Baum (1993) *C&EN*, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like). In one preferred embodiment, a chemical scaffold of any of the chemical entities noted herein are varied by addition of the various R groups noted on the moieties to produce libraries of chemically related molecules.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well-known robotic systems have also been developed for solution phase chemistries, which can be used for combinatorial synthesis. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic manual synthetic operations performed by a chemist, and the Venture™ platform, an ultra-high-throughput synthesizer that can run between 576 and 9,600 simultaneous reactions from start to finish (see, Advanced ChemTech, Inc. Louisville, Ky.)). Microfluidic approaches can also be used for library generation and screening, e.g., using a microfluidic device comprising an interface that can access standard microtiter plates, or that can access arrays of dried reagents such as the LibraryCard™ from Caliper Technologies, Corp. (Mountain View, Calif.). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Agonist Databases

In certain embodiments, agents that score positively in the assays described herein (e.g. show an ability to modulate nuclear receptor-dependent gene expression) can be entered into a database of putative and/or actual agonists. The term database refers to a means for recording and retrieving information (e.g., a computer comprising database software, or a manual database). In preferred embodiments, the database also provides means for sorting and/or searching the stored information (e.g., appropriate software or an appropriate index). The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to personal computer systems, mainframe systems, distributed nodes on an inter- or intra-net, data or databases stored in specialized hardware (e.g., in microchips), and the like. As mentioned above, the database can include an inventory tracking/storage/control system that tracks agonists, complexes, libraries, library members, or mixed library members, as described herein.

Treatment and Pharmaceutical Compositions

A wide variety of disease conditions are treatable with appropriate nuclear receptor agonists. These include hyperchloesterolemia, atherosclerosis, obesity, cardiac arrhythmia, modulation of reproductive organ function, hypothyroidism, osteoporosis, hypertension, cancer (e.g., thyroid cancer, breast cancer, prostate cancer, etc.) glaucoma, and depression.

In general, a therapeutically effective amount of the agonist is administered over time. In therapeutic use, the compounds of the present invention are usually administered in a standard pharmaceutical formulation. The present invention therefore provides pharmaceutical compositions comprising an agonist of the invention (or deliverable form thereof, such as a pharmaceutically acceptable salt) and a pharmaceutically acceptable carrier. Pharmaceutical administration methods include those that bring the composition into contact with a target tissue or fluid, e.g., via oral, intravenous, parenteral, topical (including ocular), or rectal administration.

In general, pharmaceutically useful substances identified by the methods of this invention can be useful in the form of the free acid, in the form of a salt and/or as a hydrate. All forms are within the scope of the invention. Basic salts can be formed and are a convenient form for use; in practice, use of the salt form inherently amounts to use of the acid form. The bases which can be used to prepare the salts include preferably those which produce, when combined with the free acid, pharmaceutically acceptable salts, that is, salts whose anions are non-toxic to the animal organism in pharmaceutical doses of the salts, so that the beneficial properties inherent in the free acid are not vitiated by side effects ascribable to the cations. Although pharmaceutically acceptable salts of the acid compound are preferred, all salts are useful as sources of the free acid form even if the particular salt per se is desired only as an intermediate product as, for example, when the salt is formed only for purposes of purification and identification, or when it is used as an intermediate in preparing a pharmaceutically acceptable salt by ion exchange procedures.

In any case, the agonists of the invention can be administered to a mammalian host in a variety of formats, e.g., they can be combined with various pharmaceutically acceptable inert carriers in the form of tablets, capsules, lozenges, troches, hard candies, powders, sprays, elixirs, syrups, injectable or eye drop solutions (e.g., for treatment of glaucoma), or in ocular implants or contact lenses and/or the like depending on the chosen route of administration, e.g., orally, topically, or parenterally. Parenteral administration in this respect includes administration by the following routes: intravenous, intramuscular, subcutaneous, intraocular, intrasynovial, transepithelial (including transdermal, ophthalmic, sublingual and buccal), topical (including ophthalmic, dermal, ocular, rectal, nasal inhalation via insufflation and aerosol), and rectal systemic. Oral administration is one preferred route of administration.

Active compounds can be orally administered, for example, with an inert diluent or with an assimilable edible carrier, or it can be enclosed in hard or soft shell gelatin capsules, or it can be compressed into tablets, or it can be incorporated directly with food in the diet. For oral therapeutic administration, the active compound can be incorporated with excipient and used in the form of ingestible tablets, buccal tablets, troches, capsules, elixirs, suspensions, syrups, wafers, and the like. Such compositions and preparations should contain at least 0.1% of active compound (agonist). The percentage of the compositions and preparations can, of course, be varied and can conveniently be, e.g., between about 2 and about 20% of the weight of the unit. The amount of active compound in such therapeutically useful compositions is such that a suitable dosage will be obtained. Preferred compositions or preparations according to the present invention are prepared so that an oral dosage unit form contains between about 0.05 and 1000 mg of active compound.

One advantage of a tablet or a capsule is that the patient can easily self-administer unit doses. In general, unit doses contain, e.g., in the range of from 0.05-100 mg of a given agonist. The active ingredient can be administered, e.g., from 1 to about 10 times a day. Thus daily doses are in general in the range of from 0.05 to 1000 mg per day.

The tablets, troches, pills, capsules and/or the like can also contain the following: a binder such as polyvinylpyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed. In addition, the active compound can be incorporated into sustained-release preparations and formulations.

The active compound can also be administered parenterally or intraperitoneally. For purposes of parenteral administration, solutions in sesame or peanut oil or in aqueous propylene glycol can be employed, as well as sterile aqueous solutions of the corresponding water-soluble, alkali metal or alkaline-earth metal salts. Such aqueous solutions should be suitably buffered, if necessary, and the liquid diluent first rendered isotonic with sufficient saline or glucose. Solutions of the active compound as a free base or a pharmacologically acceptable salt can be prepared in water suitably mixed with a surfactant such as hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration, though this can vary depending on the solubility of the agonist, the desired dose and the like), otherwise similar to the above parenteral solutions, are prepared in containers suitable for drop-wise administration to the eye. The therapeutic compounds of this invention can be administered to a mammal alone or in combination with pharmaceutically acceptable carriers. As noted above, the relative proportions of active ingredient and carrier are determined by the solubility and chemical nature of the compound, chosen route of administration and standard pharmaceutical practice. The dosage of the agonists that are most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. Oral administration generally uses higher dosages. The compounds are administered either orally or parenterally, or topically as eye drops or via an ocular insert (e.g., an agonist impregnated contact lens). Dosages can readily be determined by physicians using methods known in the art, using dosages typically determined from animal studies or available agonist therapies as starting points.

Where the agonist is used in combination with another therapeutic agent, the effective amount of the agonist can, in some circumstances, be lower than the effective amount of agonist administered without the additional therapeutic. The delivery method can also vary depending on what is co administered with the agonist.

In general, the typical daily dose of agonist of the invention varies according to individual needs, the condition to be treated and with the route of administration. Suitable doses are typically in the general range of from 0.001 to 10 mg/kg bodyweight of the recipient per day. Within this general dosage range, doses can be chosen at which the agonists have desired effects, e.g., which lower plasma cholesterol levels and raise metabolic rate with little or no direct effect on the heart. In general, such doses will be in the range of from lower doses (0.001 to 0.5 mg/kg) to higher doses (0.5 to 10 mg/kg). Similarly, within the general dose range, doses can be chosen at which the agonists lower plasma cholesterol levels and have little or no effect on the heart without raising metabolic rate. In general, but not exclusively, such doses will be in the range of from 0.001 to 0.5 mg/kg. It is to be understood that the sub ranges noted above are not mutually exclusive and that the particular activity encountered at a particular dose will depend on the nature of the agonist used.

Receptor Assays

The methods of this invention have immediate utility in screening for agonists that modulate, e.g., activate, a nuclear receptor, e.g., in a container, in a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred PCR conditions), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it can be desired to assay protein concentration. Conversely, where it is desired to screen for agonists that alter transcription of a nuclear receptor responsive gene or a nucleic acid having a nuclear receptor response element, nucleic acid based assays are preferred.

Routine selection and optimization of assay formats is well known to those of ordinary skill in the art.

Assays for Monitoring Nuclear Receptor Activation

In certain embodiments, this invention provides methods of producing, identifying and designing agonists that activate nuclear receptors. The methods can involve confirming or testing, e.g., by screening, an agent for activity that modulates the effect(s), e.g., as described herein (e.g., agonist activity), of an activated receptor, e.g., in a mammalian cell.

Thus, in certain embodiments, the screening methods of this invention can involve contacting a mammalian test cell with a test agent (e.g., a putative agonist, or an agonist depending on the application); and detecting the expression or activity of a nuclear receptor responsive gene (NRRG) of said test cell wherein a difference in NRRG expression or activity in said test cell as compared to nuclear receptor responsive gene expression or activity in a control cell indicates that said test agent modulates the effect of the nuclear receptor. In certain embodiments, the screening methods can also involve detecting alterations of the subcellular location of a protein in a cell exposed to the test agent and/or detecting cellular events associated (e.g. protein phosphorylation, gene expression, protein conformation change, protein association, dimerization etc.) with the test agent.

Expression levels of a gene can be altered by changes in the transcription of the gene product (i.e. transcription of mRNA), and/or by changes in translation of the gene product (i.e. translation of the protein), and/or by post-translational modification(s) (e.g. protein folding, glycosylation, etc.). Assays of this invention include assaying for level of transcribed mRNA (or other nucleic acids derived from nucleic acids that encode a polypeptide comprising a nuclear receptor responsive gene), level of translated protein, activity of translated protein, etc. Examples of such approaches are described below. These examples are intended to be illustrative and not limiting.

Nucleic-Acid Based Assays.

Target Molecules.

Changes in expression levels of a NRRG can be detected by measuring changes in mRNA and/or a nucleic acid derived from the mRNA (e.g. reverse-transcribed cDNA, etc.) that encodes a polypeptide of the gene product of NRRG or a gene product of a nucleic acid that has a nuclear responsive element. In order to measure the NRRG expression level, it is desirable to provide a nucleic acid sample for such analysis. In preferred embodiments, the nucleic acid is found in or derived from a biological sample. The term "biological sample", as used herein, refers to a sample obtained from an organism or from components (e.g., cells) of an organism, or of a cell or of a tissue culture.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

In a preferred embodiment, the "total" nucleic acid is isolated from a given sample using, for example, an acid guanidinium-phenol-chloroform extraction method and polyA+ mRNA is isolated by oligo dT column chromatography or by using $(dT)_n$ magnetic beads (see, e.g., Sambrook et al., *Molecular Cloning: A Laboratory Manual (3rd ed.)*, Vols. 1-3, Cold Spring Harbor Laboratory, (2001), or *Current Protocols in Molecular Biology*, F. Ausubel et al., ed. Greene Publishing and Wiley-Interscience, New York (1997 and supplemented through 2002)).

Frequently, it is desirable to amplify the nucleic acid sample prior to assaying for expression level. Methods of amplifying nucleic acids are well known to those of skill in the art and include, but are not limited to polymerase chain reaction (PCR, see, e.g., Innis, et al., (1990) *PCR Protocols. A guide to Methods and Application*. Academic Press, Inc. San Diego,), ligase chain reaction (LCR) (see Wu and Wallace (1989) *Genomics* 4: 560, Landegren et al. (1988) *Science* 241: 1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In one embodiment, where it is desired to quantify the transcription level (and thereby expression) of NRRG in a sample, the nucleic acid sample is one in which the concentration of the NRRG mRNA transcript(s), or the concentration of the nucleic acids derived from the NRRG polypeptide mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required, appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, the sample comprises a nucleic acid comprising a NRRG encoded polypeptide in the total mRNA or a total cDNA isolated and/or otherwise derived from a biological sample. The nucleic acid can be isolated from the sample according to any of a number of methods well known to those of skill in the art as indicated above.

Hybridization-Based Assays.

Using the known nucleic acid sequences encoding polypeptides encoded by NRRG, detecting and/or quantifying transcript(s) of these nucleic acids can be routinely accomplished using nucleic acid hybridization techniques (see, e.g., Sambrook et al. supra). For example, one method for evaluating the presence, absence, or quantity of reverse-transcribed cDNA involves a "Southern Blot." Alternatively, the mRNA can be directly quantified in a Northern blot. An alternative means for determining the NRRG expression level is in situ hybridization. In situ hybridization assays are well known (e.g., Angerer (1987) *Meth. Enzymol* 152: 649). The reagent used in in situ hybridization assays and the conditions for use vary depending on the particular application. In some applications it is necessary to block the hybridization capacity of repetitive sequences. Thus, in some embodiments, tRNA, human genomic DNA, or Cot-I DNA is used to block non-specific hybridization.

Amplification-Based Assays.

In another embodiment, amplification-based assays can be used to measure NRRG expression (transcription) level. In such amplification-based assays, the target nucleic acid sequences (i.e., a nucleic acid comprising a NRRG encoded polypeptide or fragment thereof) act as template(s) in amplification reaction(s) (e.g. Polymerase Chain Reaction (PCR) or reverse-transcription PCR (RT-PCR)). In a quantitative amplification, the amount of amplification product will be proportional to the amount of template (e.g., NRRG polypeptide-encoding mRNA) in the original sample. Comparison to appropriate (e.g. healthy tissue or cells unexposed to the test agent) controls provides a measure of the transcript level.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that can be used to calibrate the PCR reaction. Kits utilizing Taqman Tm probes and/or molecular beacons are commonly available for performing real time PCR analysis, and can be used for these applications in the present invention.

Hybridization Formats and Optimization of Hybridization Conditions.

a) Array-Based Hybridization Formats.

In one embodiment, the methods of this invention can be utilized in array-based hybridization formats. Arrays have a multiplicity of different "probe" or "target" nucleic acids (or other compounds), e.g., attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other. Methods of performing hybridization reactions in array based formats are well known to those of skill in the art (see, e.g., Pastinen (1997) *Genome Res.* 7: 606-614; Jackson (1996) *Nature Biotechnology* 14:1685; Chee (1995) *Science* 274: 610; WO 96/17958, Pinkel et al. (1998) *Nature Genetics* 20: 207-211). See also U.S. Pat. No. 5,807,522, U.S. Pat. No. 5,143,854, U.S. Pat. No. 5,744,305, U.S. Pat. No. 5,744,305 U.S. Pat. No. 5,800,992, U.S. Pat. No. 5,445,934 and PCT Patent Publication Nos. WO 90/15070 and 92/10092 b) Other Hybridization Formats.

As indicated above, a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587. Typically, labeled signal nucleic acids are used to detect hybridization. Complementary nucleic acids or signal nucleic acids can be labeled by any one of several methods typically used to detect the presence of hybridized polynucleotides as described herein.

The sensitivity of the hybridization assays can be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems.

c) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions can be selected to provide any degree of stringency. Hybridization specificity can be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array can be washed at successively higher stringency solutions and read between each wash. Analysis of the data sets thus produced will reveal a wash stringency above which the hybridization pattern is not appreciably altered and which provides adequate signal for the particular probes of interest.

Optionally, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105-114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

d) Labeling and Detection of Nucleic Acids.

The probes used herein for detection of NRRG expression levels can be full length or less than the full length of the polypeptides comprising the NRRG encoded protein. Shorter probes are empirically tested for specificity. Preferred probes are sufficiently long so as to specifically hybridize with the target nucleic acid(s) under stringent conditions. The preferred size range is from about 20 bases to the length of the target mRNA, more preferably from about 30 bases to the length of the target mRNA, and most preferably from about 40 bases to the length of the target mRNA.

The probes are typically labeled, with a detectable label. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another.

Suitable chromogens that can be employed include those molecules and compounds which absorb light in a distinctive range of wavelengths so that a color can be observed or, alternatively, which emit light when irradiated with radiation of a particular wave length or wave length range, e.g., fluorescers.

Detectable signal can also be provided by chemiluminescent and bioluminescent sources. Chemiluminescent sources include a compound that becomes electronically excited by a chemical reaction and can then emit light which serves as the detectable signal or donates energy to a fluorescent acceptor. Alternatively, luciferins can be used in conjunction with luciferase or lucigenins to provide bioluminescence.

Spin labels are provided by reporter molecules with an unpaired electron spin, which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label can be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid can be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label can be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science*, 281: 2013-2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016-2018).

Polypeptide-Based Assays.

Assay Formats

In addition to, or in alternative to, the detection of nucleic acid expression level(s), alterations in expression or activity of a NRRG encoded protein can be detected and/or quantified by detecting and/or quantifying the amount and/or activity of a translated NRRG encoded polypeptide.

Detection of Expressed Protein

The polypeptide(s) comprising a NRRG encoded protein can be detected and quantified by any of a number of methods well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, a NRRG encoded polypeptide is detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.). In another preferred embodiment, Western blot (immunoblot) analysis is used to detect and quantify the presence of a NRRG encoded protein. Many other applicable methods are described in Walker (1998), below.

The antibodies specifically bind to the target polypeptide(s) and can be directly labeled or alternatively can be subsequently detected using labeled antibodies (e.g., labeled sheep anti-mouse antibodies) that specifically bind to a domain of the antibody.

In certain embodiments, a NRRG encoded polypeptide is detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376, 110; 4,517,288; and 4,837,168) are well suited to detection or quantification of the polypeptide(s) identified herein. For a review of the general immunoassays, see also Asai (1993) *Methods in Cell Biology Volume* 37: *Antibodies in Cell Biology*, Academic Press, Inc. New York; Stites & Terr (1991) Basic and Clinical Immunology 7th Edition.

Immunological binding assays (or immunoassays) typically utilize a "capture agent" to specifically bind to and often immobilize the analyte (NRRG encoded polypeptide(s)). In preferred embodiments, the capture agent is an antibody.

Immunoassays also often utilize a labeling agent to specifically bind to and label the binding complex formed by the capture agent and the analyte. The labeling agent can itself be one of the moieties comprising the antibody/analyte complex. Thus, the labeling agent can be a labeled polypeptide or a labeled antibody that specifically recognizes the already bound target polypeptide. Alternatively, the labeling agent can be a third moiety, such as another antibody, that specifically binds to the capture agent/polypeptide complex.

Other proteins capable of specifically binding immunoglobulin constant regions, such as protein A or protein G can also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) J. Immunol., 135: 2589-2542).

Preferred immunoassays for detecting the target polypeptide(s) are either competitive or noncompetitive. Noncompetitive immunoassays are assays in which the amount of captured analyte is directly measured. In one preferred "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (NRRG encoded polypeptide) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one embodiment, the antibody is immobilized on a solid substrate. The amount of target polypeptide bound to the antibody can be determined either by measuring the amount of target polypeptide present in a polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind NRRG encoded polypeptide(s), either alone or in combination. In the case where the antibody that binds the target polypeptide(s) is not labeled, a different detectable marker, for example, an enzyme-labeled antibody capable of binding to the monoclonal antibody which binds the target polypeptide, can be employed. Any of the known modifications of EIA, for example, enzyme-linked immunoabsorbent assay (ELISA), can also be employed. As indicated above, also contemplated by the invention are immunoblotting immunoassay techniques such as western blotting employing an enzymatic detection system.

The immunoassay methods of the invention can also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely, depending on various factors such as the concentration of antigen in the sample, the nature of the sample, the type of immunoassay employed and the like. Optimal conditions can be readily established by those of ordinary skill in the art. In certain embodiments, the amount of antibody that binds NRRG encoded polypeptide(s) is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, can be employed, and other reagents such as salt to enhance ionic strength, proteins such as serum albumins, stabilizers, biocides and non-ionic detergents can also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein are commercially available or can be produced as described below.

Antibodies to NRRG Encoded Polypeptides and Activated Nuclear Receptors.

Either polyclonal or monoclonal antibodies can be used in the immunoassays of the invention described herein, e.g., for the detection of NRRG encoded polypeptides, or for the detection of the nuclear receptor agonist complexes herein. The techniques used to develop polyclonal antibodies are known in the art (see, e.g., *Methods of Enzymology*, "*Production of Antisera With Small Doses of Immunogen: Multiple Intradermal Injections*", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies see, for example, Coligan, et al. (1991) *Unit 9, Current Protocols in Immunology*, Wiley Interscience).

Antibodies produced can also be monoclonal antibodies ("mAb's"). The term "antibody" as used in this invention includes intact molecules as well as fragments thereof, such as, Fab and F(ab')$_2$', and/or single-chain antibodies (e.g. scFv) which are capable of binding an epitopic determinant. Also, in this context, the term "mab's of the invention" refers, e.g., to monoclonal antibodies with specificity for a NRRG encoded polypeptide or a nuclear receptor agonist complex. The general method used for production of hybridomas secreting mAbs is well known (Kohler and Milstein (1975) *Nature,* 256:495).

Antibodies fragments, e.g. single chain antibodies (scFv or others), can also be produced/selected using phage display technology. See, e.g., McCafferty et al. (1990) *Nature,* 348: 552-554; and, Hoogenboom et al. (1991) *Nucleic Acids Res.* 19: 4133-4137

Human antibodies can be produced without prior immunization by displaying very large and diverse V-gene repertoires on phage. See, e.g., Marks et al. (1991) *J. Mol. Biol.* 222: 581-597. In one embodiment natural VH and VL repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins. See, e.g., Marks et al. (1991) *J. Mol. Biol.* 222: 581-597; Marks et al. (1993). *Bio/Technology.* 10: 779-783; Griffiths et al. (1993) *EMBO J.* 12: 725-734; and, Clackson et al. (1991) *Nature.* 352: 624-628. Antibodies have been produced against self proteins, including human thyroglobulin, immunoglobulin, tumor necrosis factor and CEA (Griffiths et al. (1993) *EMBO J.* 12: 725-734). It is also possible to isolate antibodies against cell surface antigens by selecting directly on intact cells. The antibody fragments are highly specific for the antigen used for selection and have affinities in the 1:M to 100 nM range (Marks et al. (1991) *J. Mol. Biol.* 222: 581-597; Griffiths et al. (1993) EMBO J. 12: 725-734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

Assay Optimization.

The assays of this invention have immediate utility in screening for agents that modulate the NRRG expression and/or activity in a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred PCR conditions, protein column conditions, protein association conditions, etc.), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it can be desired to assay protein concentration. Conversely, where it is desired to screen for modulators that alter transcription of a NRRG, nucleic acid based assays are preferred.

Routine selection and optimization of assay formats is well known to those of ordinary skill in the art.

Pre-Screening for Test Agents that Bind a Nuclear Receptor.

In certain embodiments it is desired to pre-screen test agents for the ability to interact with (e.g. specifically bind to) a nuclear receptor. Specifically, binding test agents are more likely to interact with and thereby modulate NRRG expression and/or activity through (directly or indirectly) through the activated receptor. Thus, in some preferred embodiments, the test agent(s) are pre-screened for binding to nuclear receptor before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In preferred binding assays, the nuclear receptor is immobilized and exposed to a test agent (which can be labeled), or alternatively, the test agent(s) are immobilized and exposed to a nuclear receptor. The immobilized moiety is then washed to remove any unbound material and the bound test agent or bound nuclear receptor (e.g. by detection using an assay herein, by detection of a label attached to the bound molecule, or others known to one of skill in the art). The amount of immobilized label is proportional to the degree of binding between the nuclear receptor and the test agent.

Scoring the Assay(s).

The assays of this invention are scored according to standard methods well known to those of skill in the art. The assays of this invention are typically scored as positive where there is a difference between the activity seen with the test agent present or where the test agent has been previously applied, and the (usually negative) control. In certain preferred embodiments, the change/difference is a statistically significant change/difference, e.g. as determined using any statistical test suited for the data set provided (e.g. t-test, analysis of variance (ANOVA), semiparametric techniques, non-parametric techniques (e.g. Wilcoxon Mann-Whitney Test, Wilcoxon Signed Ranks Test, Sign Test, Kruskal-Wallis Test, etc.). Preferably the difference/change is statistically significant at a greater than 80%, preferably greater than about 90%, more preferably greater than about 98%, and most preferably greater than about 99% confidence level. Most preferred "positive" assays show at least a 1.2 fold, preferably at least a 1.5 fold, more preferably at least a 2 fold, and most preferably at least a 4 fold or even a 10-fold difference from the negative control.

High Throughput Screening

Any of the assays for compounds modulating the activation of a nuclear receptor described herein are amenable to high throughput screening. Preferred assays detect increases or decreases in NRRG transcription and/or translation in response to the presence of a test compound.

The cells utilized in the methods of this invention need not be contacted with a single test agent at a time. To the contrary, to facilitate high-throughput screening, a single cell can be contacted by at least two, preferably by at least 5, more preferably by at least 10, and most preferably by at least 20 test compounds. If the cell scores positive, it can be subsequently tested with a subset of the test agents until the agents having the activity are identified.

High throughput assays for various reporter gene products are well known to those of skill in the art. For example, multi-well fluorimeters are commercially available (e.g., from Perkin-Elmer). In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols of the various high throughputs. Thus, for example, Zymark Corp. provides technical bulletins describing screening systems for detecting the modulation of gene transcription, ligand binding, and the like.

Assays Relating to Alteration of Cellular Location of a Nuclear Receptor Exposed to an Agonist Using the techniques described herein, one of skill in the art can identify nuclear receptors that enter the nucleus in response to binding agonist. The localization of proteins can be determined in a variety of ways as described below. Generally, cells are examined for evidence of (1) a decrease in the amount of the protein in an origin cellular subregion; (2) an increase in the amount of the protein in a destination cellular subregion (or in an intermediate destination cellular subregion); or (3) a change in the distribution of the protein in the cellular subregions of the cell. The evidence can be direct or indirect. An example of indirect evidence is the detection of a cellular event mediated by the protein including, but not limited to, the cellular events discussed below.

Detecting Subcellular Distribution of a Protein.

Determination of the localization of the nuclear receptor (or proteins modulated by the activated nuclear receptor) can be carried out in any of a number of ways. A preferred way is by detection of a colorimetric change, for example, by visual observation. Various methods of visual observation can be used, such as light microscopy, fluorescence microscopy, and confocal microscopy. If desired, an epifluorescence microscope with a CCD camera can be used to measure translocation in the assays described below. This procedure can be automated, for example, by computer-based image recognition. The intracellular distribution of the protein can be determined by staining a cell with a stain specific for the protein. The stain comprises a specific binding substance, which binds specifically to the targeted protein. Examples of such a stain include, but are not limited to, antibodies that specifically bind to the protein. A stain specific for, e.g., a nuclear receptor can be prepared using known immunocytochemistry techniques. Stains specific for other proteins having cellular locations or quantities that can be correlated with nuclear receptor activation can be similarly prepared. Preferably, the stain further comprises a labeling moiety. Suitable antibodies can be prepared using conventional antibody production techniques. The antibodies can be monoclonal or polyclonal. Antibody fragments, such as, for example Fab fragments, Fv fragments, and the like, are also contemplated. The antibodies can also be obtained from genetically engineered hosts or from conventional sources. Techniques for antibody production are well known to the person of ordinary skill in the art and examples of such techniques can be found in Harlow and Lane, *Antibodies: A Laboratory Manual*, Cold Spring Harbor Laboratory Press, Cold Spring Harbor (1988), Birch and Lennox, *Monoclonal Antibodies: Principles and Applications*, Wiley-Liss, New York (1995). The labeling moiety will be visibly observable in conventional immunohistochemical detection techniques being, for example, a fluorescent dye such as fluorescein, a chemiluminescense reagent, a radioisotope, a colloidal label, such as colloidal gold or colored latex beads, an enzyme label, or any other known labeling complex. Such stains can be prepared by conventional techniques, for example as described in Manson (1992) *Immunochemical Protocols: Methods in Molecular Biology Vol. 10*, Humana Press, Totowa, N.J., and Beesley (1993) *Immunocytochemistry: A Practical Approach*, IRL Press, Oxford, England.

Fusion proteins can also be used to track the localization of a protein. The fusion partner can be detectable directly, such as the green fluorescent protein (GFP), or can be detected indirectly using antibodies specific for the fusion partner or by detecting the enzymatic products of a fusion partner such as β-galactosidase. Cells, which express a fusion protein, can be prepared by transfecting a host cell with a polynucleotide encoding the fusion protein. Preferably, the fusion protein is expressed at levels low enough to avoid expression in vast excess of other cellular factors, which can be required for subcellular localization of the protein. For example, if a 100-fold molar excess of the fusion protein is expressed relative to a factor required for translocation from the origin subregion to the destination subregion, translocation upon exposure to, e.g., to an agonist, cannot be detectable because most of the fusion protein would remain unbound in the origin subregion. This goal can be achieved by not using strong promoters, enhancers or origins of replication giving rise to high copy numbers of plasmids, and by transfecting with smaller amounts of DNA. Preferred fusion proteins include GFP fused to a protein for which its localization is of interest, such as, for example, nuclear receptor. GFP can be fused to either the amino terminus or the carboxy terminus of the protein of interest. A tag, such as a histidine tag, can be included, if desired.

Another preferred way to detect a calorimetric change is to use more than one stain. Preferably, the combination of the stains results in a different color than either stain alone. For example, a cell can be stained with a first stain specific for a particular cellular subregion to be examined and a second stain specific for a particular activated nuclear receptor indicative protein that migrates to or from that cellular subregion in a cell exposed to an agonist. Examples of such staining systems are known in the art and can be adapted for use in the methods described below. A preferred staining system involves the use of a fluorescence indicator, such as, for example, fluorescein, Cy3, Cy5, Texas Red, rhodamine, and the like. For example, agonist-treated cells can be stained with antibodies to nuclear receptor and secondary antibodies conjugated to fluorescein, which would stain the nuclei green. If the cells are further stained with a red nuclear-specific dye (such as, for example, TOTO-3), the nuclei with nuclear receptor will appear yellow instead of red. Other dyes for specific cellular subregions include, but are not limited to, Golgi markers such as mannosidase II and BODIPY TR ceramide (Molecular Probes), nuclear markers such as Neu N, and conjugated antibodies recognizing proteins specific to a particular subregion such as Golgi marker enzymes, histones, and the like.

The particular protein and cellular subregion(s) selected for examination can vary depending on the cell type to be used in a particular method. In one embodiment, cells used in the methods of the invention are of a cell type in which the selected protein is predominantly present in a different amount in a particular cellular subregion of agonist-exposed cells compared to agonist-unexposed cells.

Detecting Cellular Events Induced by an Agonist Activating Nuclear Receptor.

A change in the cellular localization of a protein in a cell exposed to an agonist can trigger certain cellular events that can be detected. Examples of such events include phosphorylation of substrate proteins, gene regulation, protein associations/disassociations, dimerization, conformation changes and the like. Such cellular events can be examined in a variety of ways as discussed herein and in greater detail below.

Phosphorylation.

Another aspect of the invention is to provide methods for detecting the effects of agonist activation of a nuclear receptor on cells by measuring the phosphorylation of proteins that are differentially phosphorylated in the presence and absence of activated nuclear receptor.

The identity of proteins that are differentially phosphorylated in response to nuclear receptor activation can readily be determined using conventional assay techniques known to the person of skill in the art. For example, radioactively labeled phosphate can be added to cultured cells grown in both the presence and absence of agonist. Proteins from the labeled cells can then be extracted and separated on a one or two dimensional gel system. Isolated phosphorylated proteins can then be visualized by autoradiography and related techniques. After separation and visualization, changes in the level of phosphorylation of different proteins can be determined by comparing the results obtained from cells exposed to agonist with the results obtained from cells not exposed to agonist. Preferably, proteins of interest are immunoprecipitated. Proteins that are differentially phosphorylated can be identified by amino terminus amino acid residue sequencing.

A more sensitive detection method involves the use of phosphoantibodies, for example, antibodies that recognize phosphorylated forms of specific proteins, or antibodies that recognize a phosphorylated amino acid residue, such as phosphothreonine or phosphoserine antibodies. Another useful detection method is back-phosphorylation, which is safer than direct phosphorylation assays but less sensitive. Cell extracts are incubated with radiolabeled ATP and Mg++ and subjected to gel electrophoresis. Since agonist can alter phosphorylation, a different amount of radiolabeled phosphate will be incorporated into individual proteins of cells exposed to an agonist than in cells that have not been so exposed, resulting in a different pattern of bands on a gel.

Proteins that are differentially phosphorylated in response to cellular agonist exposure can be used in assays for the exposure of cells to agonist. Furthermore, these differentially phosphorylated proteins can be used as the targets when screening for compounds that modulate the cellular effects of nuclear receptor activation. Such assays include assays involving the steps of measuring the phosphorylation of differentially phosphorylated proteins. Compounds could be screened by measuring their effects on phosphorylation of these differentially phosphorylated proteins. Phosphorylation of such proteins by activation of nuclear receptor in response to cellular exposure to agonist can be determined in a variety of ways known in the art, such as, for example, by using phospho-specific antibodies.

Gene Expression

Some proteins which are localized differently in cells exposed to agonist, which activates a nuclear receptor can affect gene regulation, either directly or indirectly. For purposes of the methods described below, the gene is preferably regulated by an activated nuclear receptor (whether directly or indirectly).

Gene transcription modulated by nuclear receptor activation by an agonist of the invention can be monitored by assays known to one of skill in the art and those described herein. For example, at least one nuclear receptor responsive gene and/or a nuclear receptor response element, e.g., thyroid hormone response element (TRE), glucoocorticoid hormone response element (GRE), etc., can be coupled with a reporter gene, the expression of which is preferably controlled by an activated nuclear receptor. Control of expression by activated nuclear receptor can be enhanced by increasing the number of binding sites for an activated nuclear receptor in the vicinity of the reporter gene. Examples of reporter genes, include, but are not limited to chloramphenicol acetyl transferase (CAT) (Alton et al., *Nature* (1979) 282:864-869), beta-galactosidase, firefly luciferase (deWet et al., *Mol. Cell. Biol.* (1987) 7:725-737), bacterial luciferase (Engebrecht et al., *Proc. Natl. Acad. Sci. USA* (1984) 1:4154-4158; Baldwin et al., *Biochemistry* (1984) 23:3663-3667, alkaline phosphatase (Toh et al., *J. Biochem.* (1989) 182:231-238; Hall et al., *J. Mol. Appl. Gen.* (1983) 2: 101, and green fluorescent protein (GFP) (Meyer et al., *Diabetes* (1998) 47(12):1974-1977), a GFP-luciferase fusion protein (Day et al. *Biotechniques* 1998 25(5):848-850, 852-854, 856), and other genes encoding a detectable gene product. Detection of gene expression can be achieved in a variety of ways depending on the reporter gene used. For example, a fluorescence or chemiluminescence detection system can be used to detect expression of luciferase and GFP. A nuclear receptor response element-dependent GFP construct can be used. Alternatively, an antibody that recognizes the gene product encoded by a reporter gene can be used to detect expression of many reporter genes as well as many endogenous genes regulated by nuclear receptors. Visual observation of a calorimetric change can be used to detect expression of beta-galactosidase or alkaline phosphatase. A reporter gene can be inserted into the cells by various techniques known in the art and described herein. Transient expression is preferred. However, the reporter gene can be present on a vector that is stably integrated into the genome of the cells.

The expression of genes can be monitored by any of a number of ways known in the art and described herein, such as, for example, by Northern analysis, polymerase chain reaction (PCR), Western analysis, radioimmunoassays (RIA), enzyme linked immunoassays (ELISA or EIA), fluorescence activated cell sorting (FACS) analysis, enzyme-substrate assays such as chloramphenicol transferase (CAT) assays, and the like. Preferably, expression of such genes in response to agonist binding the nuclear receptor is determined by detecting a signal at least about 1.5 times that of control cells which have not been exposed to the agonist, preferably greater than about 2×.

Receptor Cloning and Assay Tissue Culture

In practicing the present invention, many conventional techniques in molecular biology, microbiology, and recombinant DNA are advantageously used. For example, receptors are optionally cloned and expressed, e.g., to perform in vitro or in vivo assay screens as described above. In general, these techniques are well known and are explained in, for example, *Current Protocols in Molecular Biology*, Volumes I, II, and III, 1997 (F. M. Ausubel ed.), supplemented through 2002; Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning; the series, Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology* Vol. 154 and Vol. 155 (Wu and Grossman, and Wu, eds., respectively).

Similarly, cells (e.g., mammalian, fungal, plant or animal cells) comprising receptors can be grown, e.g., using conventional culture methods. In addition to the references noted in the preceding paragraph, further details regarding tissue culture can be found, e.g., in Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Receptors are optionally purified for in vitro or in vivo use, e.g., for producing the receptor-agonist complexes of the invention. In addition to other references noted herein, a variety of purification/protein purification methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications*, Second Edition Wiley-VCH, NY; and Walker (1998) *Protein Protocols on CD-ROM* Humana Press, NJ; and the references cited therein.

Kits

Another aspect of the invention is to provide kits for carrying out the subject methods. For example, kits can include the receptor complexes of the invention, in combination with other kit components, such as packaging materials, instructions for user of the complexes or the like. Libraries can also be packaged in kits, e.g., comprising library components such as arrays in combination with packaging materials, instructions for array use or the like. Kits generally contain one or more reagents necessary or useful for practicing the methods of the invention. Reagents can be supplied in pre-measured units so as to provide for uniformity and precision in test results.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of selecting an agonist for a nuclear receptor, the method comprising:
   physically providing a modified nuclear receptor ligand comprising an extension, wherein the extension contacts a region of the nuclear receptor outside of a native ligand binding pocket of the nuclear receptor, wherein the extension of the modified nuclear receptor ligand spatially fits into the region without substantially disrupting a coactivator binding surface of the nuclear receptor; and,
   confirming via an agonist activity assay that the modified nuclear receptor ligand comprises agonist activity on the nuclear receptor, thereby selecting the agonist.

2. The method of claim 1, wherein the region comprises a domain formed by helices 3 and 11 of the nuclear receptor.

3. The method of claim 1, wherein the coactivator binding surface is formed by one or more of helices 3, 4, 5, 6 and 12 of the nuclear receptor.

4. The method of claim 1, wherein the extension comprises a —XR moiety, wherein the X is selected from the group consisting of a $CH_2$, an O, a S, a NH, a NR", a CHR", and a CR"$_2$ and Wherein R" is a H or a lower alkyl, and wherein R is selected from the group consisting of a phenyl, a 5-member heterocyclic ring, a 6-member heterocyclic ring, a substituted phenyl, a substituted 5-member heterocyclic ring, and a substituted 6-member heterocyclic ring.

5. The method of claim 1, wherein the extension is greater than about 50 Daltons and less than about 500 Daltons in size.

6. The method of claim 1, wherein the extension comprises at least 3 carbons.

7. The method of claim 1, wherein the nuclear receptor is a thyroid hormone receptor.

8. The method of claim 7, wherein the thyroid hormone receptor is a β thyroid hormone receptor.

9. The method of claim 1, wherein the nuclear receptor is selected from the group consisting of: a glucocorticoid receptor, an estrogen receptor, an androgen receptor, a mineralocorticoid receptor, a progestin receptor, a vitamin D receptor, a retinoid receptor, a retinoid X receptor, a peroxisomal proliferator activated receptor, an estrogen-receptor related receptor, a short heterodimer partner, a constitutive androstane receptor, a liver X receptor, a pregnane X receptor, a HNF-4 receptor, a farnesoid X receptor and an orphan receptor.

10. The method of claim 1, wherein the nuclear receptor comprises a nuclear receptor isoform.

11. The method of claim 1, wherein the providing comprises use of a synthesized modified nuclear receptor ligand.

12. The method of claim 1, wherein the providing comprises providing a nuclear receptor ligand and modifying the nuclear receptor ligand by coupling an extension to the receptor ligand, thereby providing the modified nuclear receptor ligand.

13. The method of claim 1, wherein the providing comprises providing a native nuclear receptor ligand and modifying the native nuclear receptor ligand by coupling an extension to the native receptor ligand, thereby providing the modified nuclear receptor ligand.

14. The method of claim 1, wherein the confirming comprises: binding the modified nuclear receptor ligand to the nuclear receptor; and, testing the resulting ligand bound nuclear receptor for agonist activity.

15. The method of claim 1, wherein the confirming is performed in vitro.

16. The method of claim 1, wherein the confirming is performed in vivo.

17. The method of claim 1, wherein the agonist activity is confirmed by testing activation of the nuclear receptor.

18. The method of claim 17, wherein activation of the nuclear receptor alters transcription of at least one nuclear receptor responsive gene.

19. The method of claim 17, wherein activation of the nuclear receptor comprises dissociation of a heat shock protein from the nuclear receptor.

20. The method of claim 17, wherein activation of the nuclear receptor comprises dimerization of the nuclear receptor.

21. The method of claim 17, wherein activation of the nuclear receptor comprises dissociation of one or more transcriptional repressor or other regulatory proteins from the nuclear receptor.

22. The method of claim 1, wherein the agonist comprises increased specificity to the nuclear receptor compared to a naturally occurring ligand of the nuclear receptor.

23. The method of claim 1, wherein the agonist displays increased affinity to the nuclear receptor compared to a naturally occurring ligand of the nuclear receptor.

24. A method of selecting an agonist for a nuclear receptor, the method comprising:
   physically providing a modified nuclear receptor ligand comprising means for contacting a region of the nuclear receptor outside of a native ligand binding pocket of the nuclear receptor, wherein an extension of the modified nuclear receptor ligand spatially fits into the region without substantially disrupting a coactivator binding surface of the nuclear receptor; and,
   confirming via an agonist activity assay that the modified nuclear receptor ligand comprises agonist activity on the nuclear receptor, thereby selecting the agonist.

* * * * *